US008103525B2

(12) United States Patent
Kelly et al.

(10) Patent No.: US 8,103,525 B2
(45) Date of Patent: Jan. 24, 2012

(54) UTILIZING CONDITIONAL LOGIC IN MEDICAL DOCUMENTATION

(75) Inventors: Lisa Kelly, Overland Park, KS (US); Mary Gannon, Shawnee, KS (US)

(73) Assignee: Cerner Innovation, Inc., Overland Park, KS (US)

( * ) Notice: Subject to any disclaimer, the term of this patent is extended or adjusted under 35 U.S.C. 154(b) by 397 days.

(21) Appl. No.: 12/351,448

(22) Filed: Jan. 9, 2009

(65) Prior Publication Data

US 2010/0179818 A1 Jul. 15, 2010

(51) Int. Cl.
*G06Q 50/00* (2006.01)

(52) U.S. Cl. .......................................................... 705/2

(58) Field of Classification Search .................. 705/2, 3; 600/437

See application file for complete search history.

(56) References Cited

U.S. PATENT DOCUMENTS

2002/0091548 A1* 7/2002 Auer et al. ........................ 705/3
2002/0198454 A1* 12/2002 Seward et al. ................ 600/437
2003/0220819 A1* 11/2003 Burstein et al. .................... 705/3
2008/0065420 A1* 3/2008 Tirinato et al. ................... 705/3

* cited by examiner

*Primary Examiner* — Gerald J. O'Connor
*Assistant Examiner* — John Pauls
(74) *Attorney, Agent, or Firm* — Shook, Hardy & Bacon L.L.P.

(57) ABSTRACT

Methods, computer storage media, systems and user interfaces that guide a clinician to complete medical documentation. The method, computer storage media, system and user interfaces include presenting a first medical documentation set to indicate a medical aspect for which medical data is to be documented. At least one of the medical documentation elements in the first set is linked to a second medical documentation set. A selection of one of the linked medical documentation elements in the first set is received, and the second medical documentation set is presented. An attribute for at least one of the medical data fields in the first or second set is received, and the attributes received for the first and the second medical documentation sets are aggregated into a medical data group.

19 Claims, 18 Drawing Sheets

□ ADAMS, CHARLES
TASK EDIT VIEW PATIENT CHART LINKS HELP
□ PAL ▤ STAFF ⚷ PATIENT ▣ INBOX ▣ BASELINE WEST

ADAMS, CHARLES 57 Y M    ALLERGIES: CODINE    VISIT REASON: CHEST PAIN    VISIT DATE: 02/06/2006    IQHEALTH: YES
DOB: 04/02/1949  MRN:00-00-0989    FIN: 005436    LOCATION: 306A    PCP: JOHN JONES MD

|VIEW/I&O| | | | |
|---|---|---|---|---|
| | |FEBRUARY 6, 2007 11:36: AM FEBRUARY 09, 2007 11:59 AM| | |
|▨ CRITICAL CARE|FIND ITEM ▼|□ CRITICAL □ HIGH □ LOW □ ABNORMAL □ FLAG □ NEW □ UNAUTH| | |
|▨ GRAPHICS| | | | |
|▨ LABORATORY| | |0900|0700|
|▨ LINES AND PROC...| | |326 ⌐327|320|
|▨ MODERATE SEDA...|□ RESPIRATORY ASSESSMENT| | | |
|▨ ADULT FREQUENT...|□ RESPIRATORY|DIFFICULTY BREATH...|DIFFICULTY BREATH...|DIFFICUL|
|▨ ADULT ICU ONGOI...|RESPIRATORY SYMPTOMS|PURSED LIPS...|PURSED LIPS... 26~322|PURSED L|
|▨ INTAKE AND OUTP...—310|RESPIRATIONS  BR/MIN|26|REGULAR|REGULAR|
|▨ INTAKE AND OUTP...|RESPIRATORY RATE ⊞ 318|REGULAR|324  95| |
|▨ ACTIVITY VIEW|RESPIRATORY PATTERN|SYMMETRICAL|2| |
|▫ RESPIRATOR...—312|CHEST MOTION|92| | |
|  RESPIRATORY|OXYGEN SATURATION %|2|NON-PRODUCTIVE|NON-PF|
|▫ PATIENT SAFETY|□ OXYGEN FLOW RATE L/MIN|330| | |
|⊗ PATIENT SAFETY—314|328 AL CANNULA L/MIN| | |308|
| |◇ COUGH ☑| | | |
| |□ PATIENT SAFETY|YES|YES|YES|
| |PATIENT SAFETY|YES|YES|YES|
|316|SIDE RAILS UP|YES|YES|YES|
| |CALL LIGHT WITHIN REACH|YES|YES|YES|
| |PATIENT ID BAND ON|YES|YES|YES|
| |PATIENT ALLERGY BAND ON| | | |
| |O2 BAG/MASK AT BEDSIDE| | | |
| |BED IN LOW POSITION| | | |

302

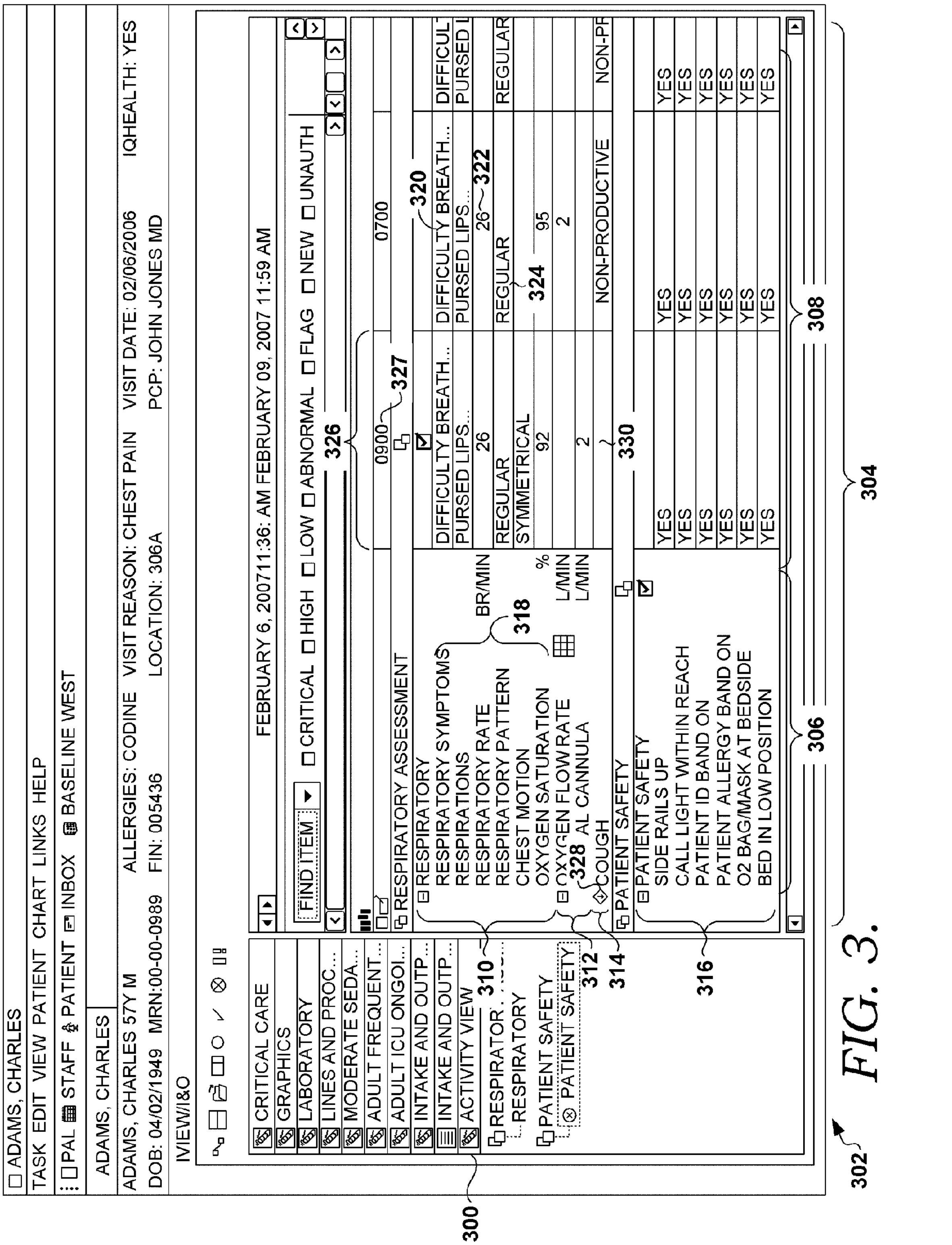

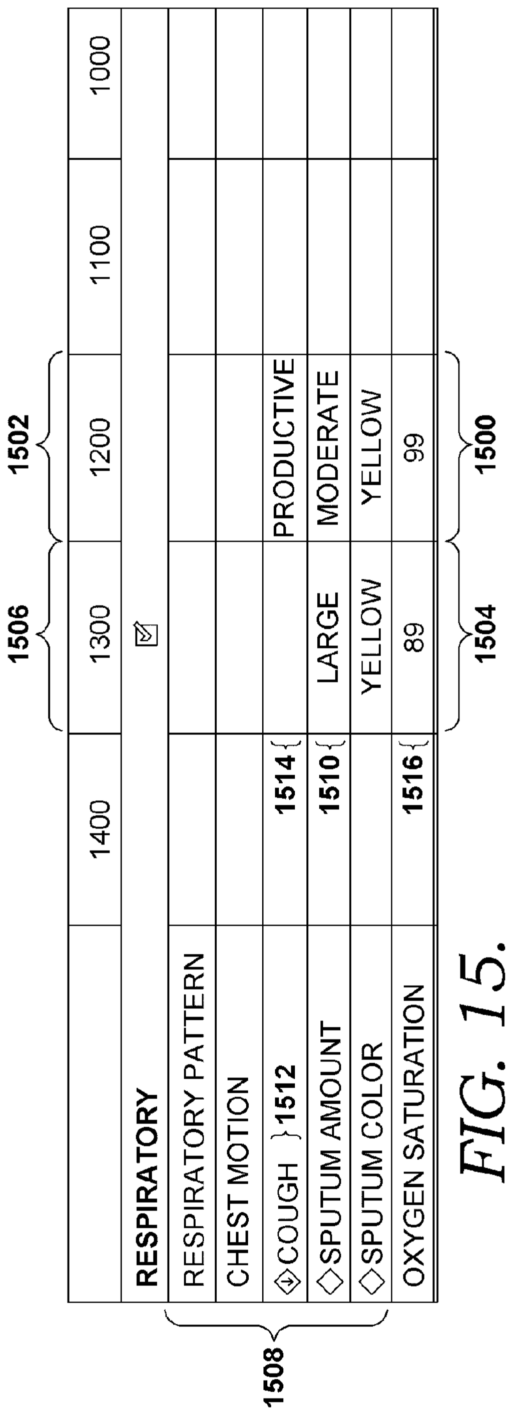

FIG. 15.

| | 1400 | 1300 | 1200 | 1100 | 1000 |
|---|---|---|---|---|---|
| **RESPIRATORY** | | | | | |
| RESPIRATORY PATTERN | | | | | |
| CHEST MOTION | | ☒ | | | |
| ◈COUGH 1512 1514 | | | PRODUCTIVE | | |
| ◇SPUTUM AMOUNT 1510 | | LARGE | MODERATE | | |
| ◇SPUTUM COLOR | | YELLOW | YELLOW | | |
| OXYGEN SATURATION 1516 | | 89 | 99 | | |

1508 { (rows) ; 1506 { 1300 } ; 1502 { 1200–1100 } ; 1504 { 89 } ; 1500 { 99 }

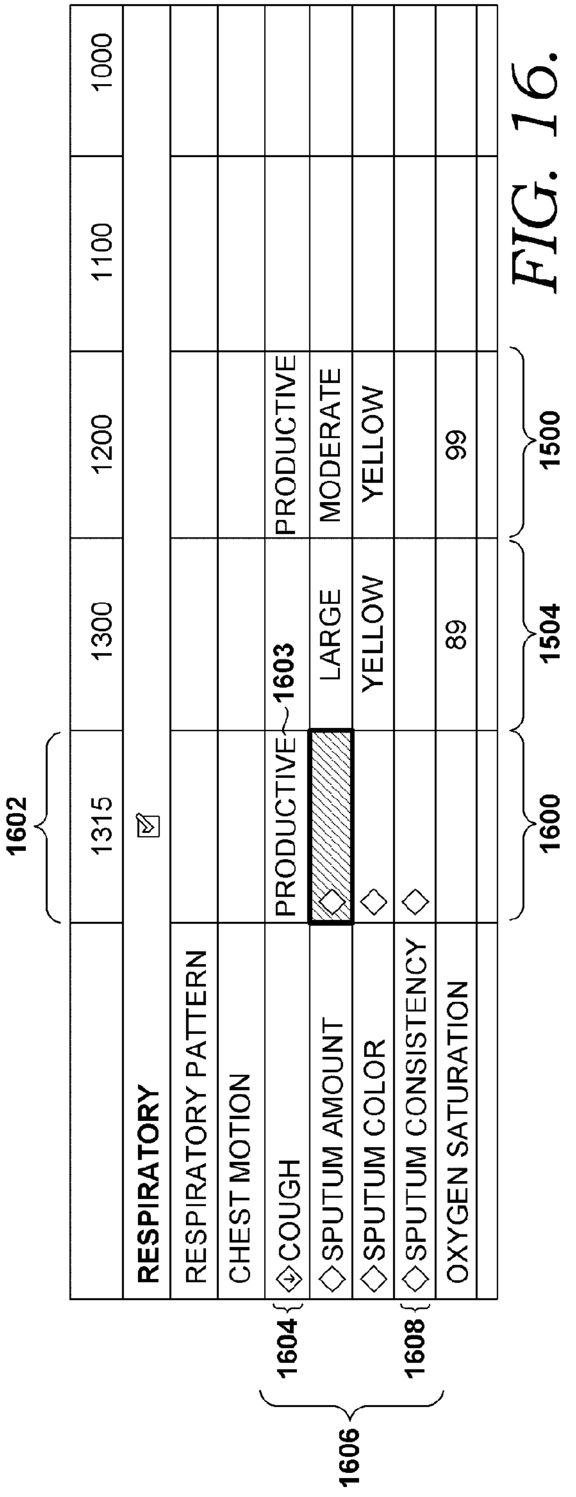

FIG. 16.

| | 1315 | 1300 | 1200 | 1100 | 1000 |
|---|---|---|---|---|---|
| **RESPIRATORY** | | | | | |
| RESPIRATORY PATTERN | | | | | |
| CHEST MOTION | ☒ | | | | |
| ◈COUGH | PRODUCTIVE~1603 | | PRODUCTIVE | | |
| ◇SPUTUM AMOUNT | ▨ | LARGE | MODERATE | | |
| ◇SPUTUM COLOR | ◇ | YELLOW | YELLOW | | |
| ◇SPUTUM CONSISTENCY | ◇ | | | | |
| OXYGEN SATURATION | | 89 | 99 | | |

1602 { 1315 } ; 1600 { data } ; 1604 { COUGH, SPUTUM AMOUNT } ; 1608 { SPUTUM COLOR, SPUTUM CONSISTENCY } ; 1606 { all rows } ; 1504 { 89 } ; 1500 { 99 }

| | 1400 | 1300 | 1200 | 1100 | 1000 |
|---|---|---|---|---|---|
| **PHYSICAL ASSESSMENT** | | | ▧ | | |
| ◇ RESP DETAILED | | | 1808 { Y | | |
| CARDIOVASCULAR DET... | | | | | |
| NEUROLOGICAL DETAI... | | | | | |
| GI DETAILED | | | | | |
| GU DETAILED | | | | | |
| MUSCULOSKELETAL D... | | | | | |
| **RESP. DETAILED** | | | ▧ | | |
| ◇ RESP DETAILED | | | Y | } 1806 | |
| ◇ CHEST MOTION | | | SYMMET... | } 1804 | |
| ◇ COUGH | | | NONPROD... | | |
| ◇ OXYGEN SATURATION | | | 97 | | |
| **CARDIOVASCULAR DETAILED** | | | ▧ | | |
| ◇ CARDIOVASCULAR D... | | | | | |

1910 1908 1906

| | 1215 | 1210 | 1200 | 1100 | 1000 |
|---|---|---|---|---|---|
| **RESPIRATORY** | | | | | |
| RESPIRATORY PATTERN | | | | | |
| CHEST MOTION | | | | | |
| 1912 ◇COUGH | PRODUCTIVE | | PRODUCTIVE | | |
| 1914 ◇SPUTUM AMOUNT | LARGE | LARGE | MODERATE | | |
| 1916 ◇SPUTUM COLOR | TAN | YELLOW | YELLOW | | |
| 1918 ◇SPUTUM CONSISTENCY | THICK | | | | |
| OXYGEN SATURATION | | | 99 | | |

| | 1215 | 1210 | 1200 | 1100 | 1000 |
|---|---|---|---|---|---|
| **RESPIRATORY** | | | | | |
| RESPIRATORY PATTERN | | | | | |
| CHEST MOTION | 2002 | | | | |
| ◇COUGH | NON PROD | | PRODUCTIVE | | |
| ◇SPUTUM AMOUNT 2004 | LARGE 2000 | LARGE | MODERATE | | |
| ◇SPUTUM COLOR 2006 | TAN | YELLOW | YELLOW | | |
| ◇SPUTUM CONSIST 2008 | THICK | | | | |
| OXYGEN SATURATION | | | 99 | | |

FIG. 20.

| | 1215 | 1210 | 1200 | 1100 | 1000 |
|---|---|---|---|---|---|
| **RESPIRATORY** | | | | | |
| RESPIRATORY PATTERN | REGULAR | | REGULAR | | |
| CHEST MOTION | SYMMETR... | | | | |
| ⬦ COUGH | NONPROD... }2100 | | NONPROD... | | |
| OXYGEN SATURATION | 97 | | 99 | | |

| | 1215 | 1210 | 1200 | 1100 | 1000 |
|---|---|---|---|---|---|
| **RESPIRATORY** | | | | | |
| RESPIRATORY PATTERN | REGULAR | | REGULAR | | |
| CHEST MOTION | SYMMETR... | | | | |
| ⬦ COUGH | PRODUCTIVE }2200 | | NONPROD... | | |
| ⬦ SPUTUM AMOUNT | ⬦ }2206 | }2204 | MODERATE | | |
| ⬦ SPUTUM COLOR | ⬦ | | YELLOW | | |
| ⬦ SPUTUM CONSISTENCY | ⬦ | | | | |
| OXYGEN SATURATION | 97 | | 99 | | |

2202

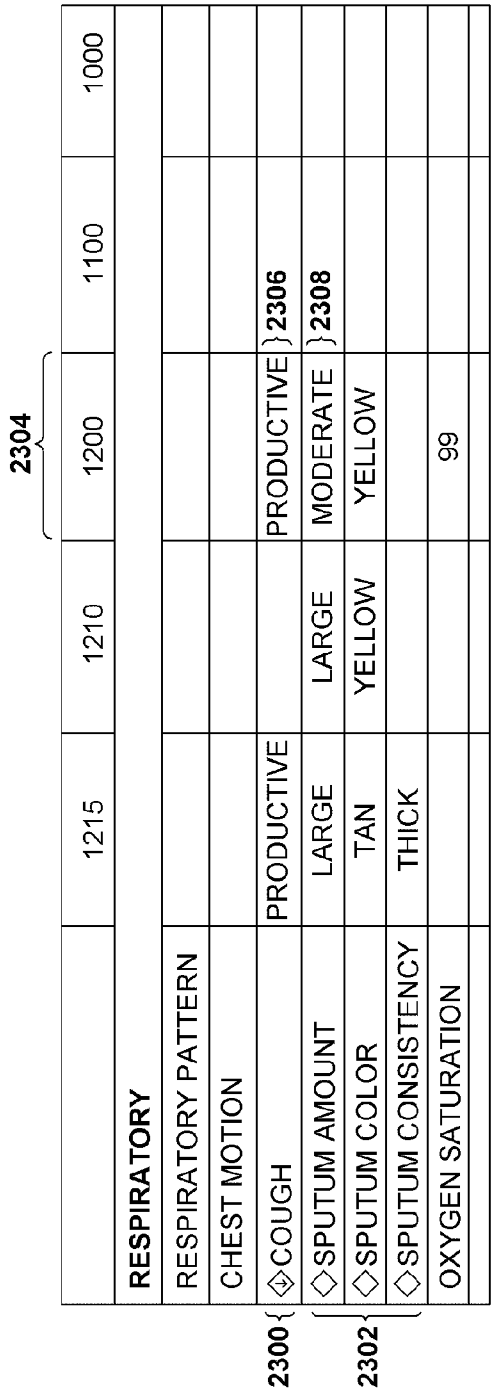

FIG. 23.

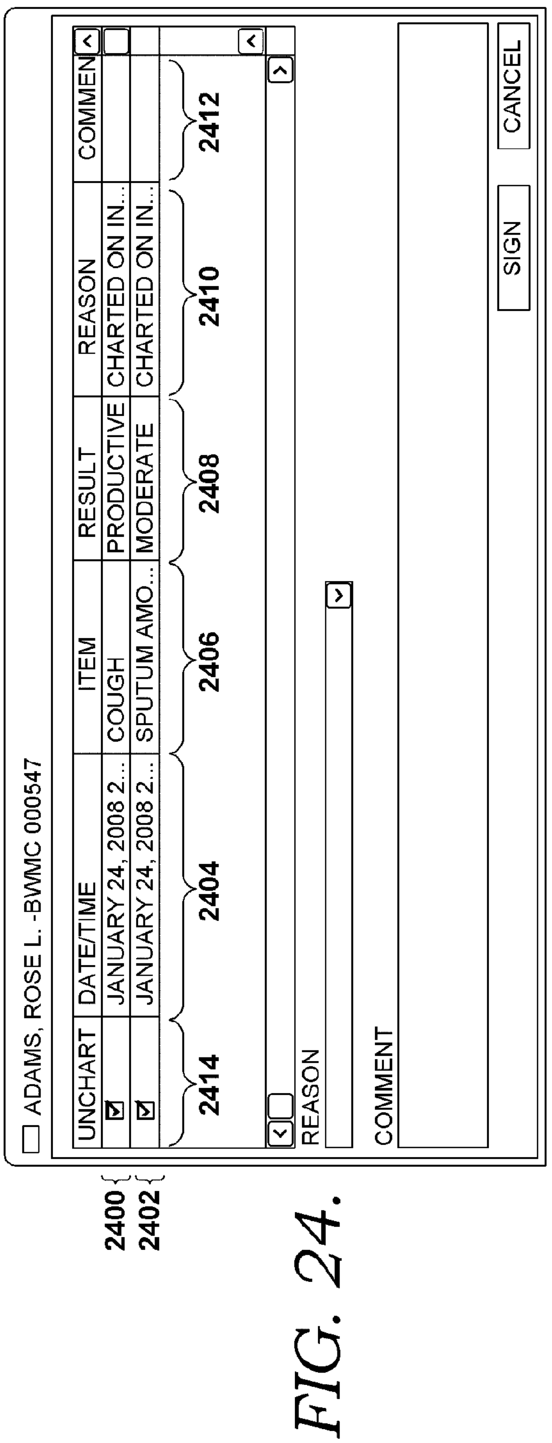

FIG. 24.

| | 1215 | 1210 | 1200 | 1100 | 1000 |
|---|---|---|---|---|---|
| **RESPIRATORY** | | | | | |
| RESPIRATORY PATTERN | | | | | |
| CHEST MOTION | | | | | |
| ◇COUGH | PRODUCTIVE | | PRODUCTIVE }2306 | | |
| ◇SPUTUM AMOUNT | LARGE | LARGE | MODERATE }2308 | | |
| ◇SPUTUM COLOR | TAN | YELLOW | YELLOW | | |
| ◇SPUTUM CONSISTENCY | THICK | | | | |
| OXYGEN SATURATION | | | 99 | | |

| UNCHART | DATE/TIME | ITEM | RESULT | REASON | COMMEN |
|---|---|---|---|---|---|
| ☑ | JANUARY 24, 2008 2:... | COUGH | PRODUCTIVE | CHARTED ON IN... | |
| ☑ | JANUARY 24, 2008 2:... | SPUTUM AMO.... | MODERATE | CHARTED ON IN... | |

2414, 2404, 2406, 2408, 2410, 2412

ADAMS, ROSE L. - BWMC 000547

2400, 2402

REASON

COMMENT

SIGN   CANCEL

| | 1215 | 1210 | 1200 | 1100 | 1000 |
|---|---|---|---|---|---|
| **RESPIRATORY** | | | | | |
| RESPIRATORY PATTERN | | | | | |
| CHEST MOTION | | | | | |
| ◇COUGH | PRODUCTIVE | | IN ERROR | }2500 | |
| ◇SPUTUM AMOUNT | LARGE | LARGE | IN ERROR | }2502 | |
| ◇SPUTUM COLOR | TAN | YELLOW | YELLOW | | |
| ◇SPUTUM CONSISTENCY | THICK | | | | |
| OXYGEN SATURATION | | | 99 | | |
| | | | | | |

*FIG. 25.*

UTILIZING CONDITIONAL LOGIC IN MEDICAL DOCUMENTATION

BACKGROUND

Medical care in association with procedures, medications, laboratory tests, evaluations, treatments, and assessments performed for a patient is oftentimes electronically documented by healthcare providers. In a clinical computing environment, a documentation section for recording medical data associated with a specific medical event may be established by a healthcare provider. The documentation section may include documentation elements and associated data fields for documenting medical events. Given the number of potential medical events, this section may include a vast number of medical elements and data fields. Presenting all of the possible combinations of medical elements and data fields to the clinician can lead to a cluttered and confusing interface thereby making it difficult to properly document the medical event. Further, some elements and data fields may be more relevant in documenting one type of medical event and less relevant in documenting a different type of medical event. However, the relevancy of the element to the specific medical event may not be apparent because the individual elements are not indicated or associated with one another.

Thus, it would be beneficial to have a system and method in a clinical computing environment that guides the clinician in completing the documentation of a medical event. Such guidance would minimize confusion about which medical documentation may be required and which documentation may be optional or not required at all. For example, it would be beneficial for a system to indicate what documentation is required for a specific medical event and display this information in a concise form. It would also be beneficial if the system and method provides the ability to see previously documented results in the context of the current documentation. This would provide initial guidance when documenting reoccurring medical events in a chronological format.

BRIEF SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Embodiments of the present invention relate to a method, in a clinical computing environment, for guiding a clinician to complete medical documentation. In one embodiment, the method includes presenting a first medical documentation set having a first set of medical documentation elements and a first set of medical data fields to indicate a medical aspect for which medical data is to be documented. The method further includes indicating that at least one of the medical documentation elements in the first set is linked to a second medical documentation set having a second set of medical documentation elements and a second set of medical data fields to indicate a medical aspect for which medical data is to be documented. In addition, the method includes receiving a selection of at least one of the linked medical documentation elements in the first set and presenting the second set of medical documentation elements and medical data fields in response to the selection. Further, the method includes receiving an attribute for at least one of the medical data fields in the first or second set and aggregating the attributes received for the first and the second medical documentation sets into a medical data group. Finally, the method includes presenting the medical data group.

The method may also include associating the medical data group with a first time stamp and displaying the medical data group. Further, the method may include duplicating the medical data group to create a second medical data group with both the medical data group and the second medical data group including medical assessment data and dynamic data. The method may further include associating the second medical data group with a second time stamp and displaying the second medical data group.

In another aspect, the present invention provides a user interface embodied on at least one computer-readable media to facilitate medical documentation. In embodiments, the user interface includes a first medical documentation set display area configured to display a first medical documentation set. The first medical documentation set includes a first set of medical documentation elements and a first set of medical data fields to indicate a medical aspect for which medical data is to be documented. The user interface also includes a trigger indicator that upon selection initiates an association between the first medical documentation set and a second medical documentation set. The user interface further includes a second medical documentation set display area configured to display a second medical documentation set. The second medical documentation set includes a second set of medical documentation elements and a second set of medical data fields associated with the first medical documentation set. In addition, the user interface includes a medical data group display area configured to receive attributes associated with the first and the second medical documentation sets and aggregate the attributes into a medical data group.

In other embodiments, the user interface may include a modification display area configured to indicate that an attribute in the medical data group was modified from an original entry. The user interface may also include a time stamp display area configured to display a plurality of medical data groups, each medical data group having an individual time stamp. In addition, the user interface may include a required field display area configured to indicate that an attribute is required for a medical data field in the first or second medical documentation set. The user interface may further include a multiple section display area configured to display a plurality of sections, with at least two of the sections having at least one first medical documentation set display area, at least one trigger display area, at least one second medical documentation set display area, and at least one medical data group display area. Finally, the user interface may include an unchart display area configured to enable a clinician to remove attributes from the medical data group display area.

BRIEF DESCRIPTION OF THE DRAWINGS

The present invention is described in detail below with reference to the attached drawing figures, wherein:

FIG. 3 is an illustrative screen display of an exemplary user interface for viewing a first medical documentation set, in accordance with an embodiment of the present invention;

FIG. 15 is an illustrative screen display of an exemplary user interface for viewing a second medical group duplicated from a first medical data group, in accordance with an embodiment of the present invention;

FIG. 16 is an illustrative screen display of an exemplary user interface for viewing a third medical group duplicated from a first or a second medical data group, in accordance with an embodiment of the present invention;

FIG. 19 is an illustrative screen display of an exemplary user interface for viewing a plurality of medical data groups, in accordance with an embodiment of the present invention;

FIG. 20 is an illustrative screen display of an exemplary user interface, in accordance with an embodiment of the present invention, that may be utilized for changing an attribute of a medical data group;

FIG. 23 is an illustrative screen display of an exemplary user interface for viewing a plurality of medical data groups, in accordance with an embodiment of the present invention;

FIG. 24 is an illustrative screen display of an exemplary user interface, in accordance with an embodiment of the present invention, that may be utilized to unchart attributes from a medical data group;

FIG. 25 is an illustrative screen display of an exemplary user interface for viewing uncharted attributes from a medical data group, in accordance with an embodiment of the present invention.

DETAILED DESCRIPTION

The subject matter of the present invention is described with specificity herein to meet statutory requirements. The description itself, however, is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

Embodiments of the present invention provide computerized methods and systems for facilitating medical documentation by utilizing conditional logic. Conditional logic generally includes determining whether a predetermined attribute exists within a medical data field. A predetermined attribute may comprise, for example, specific text (e.g., "productive"), a specific value or value range (e.g., 10 or 10-20), a symbol (e.g., +), or other data attribute. If a predetermined attribute exists within a medical data field, conditional logic provides an opportunity for further documentation by providing additional medical data fields, medical documentation elements, medical documentation sets, and the like. The additional fields may be added automatically or upon receiving an indication to provide such fields. The additional documentation fields can be presented as an extension of the initial medical documentation set or, alternatively, presented as a new medical documentation set. Such conditional logic allows a clinician the ability to efficiently document medical data that would otherwise be undocumented or require the clinician to generate a new medical template, medical documentation set, or medical data field.

Having briefly described embodiments of the present invention, an exemplary operating environment suitable for use in implementing embodiments of the present invention is described below.

Figure 1:
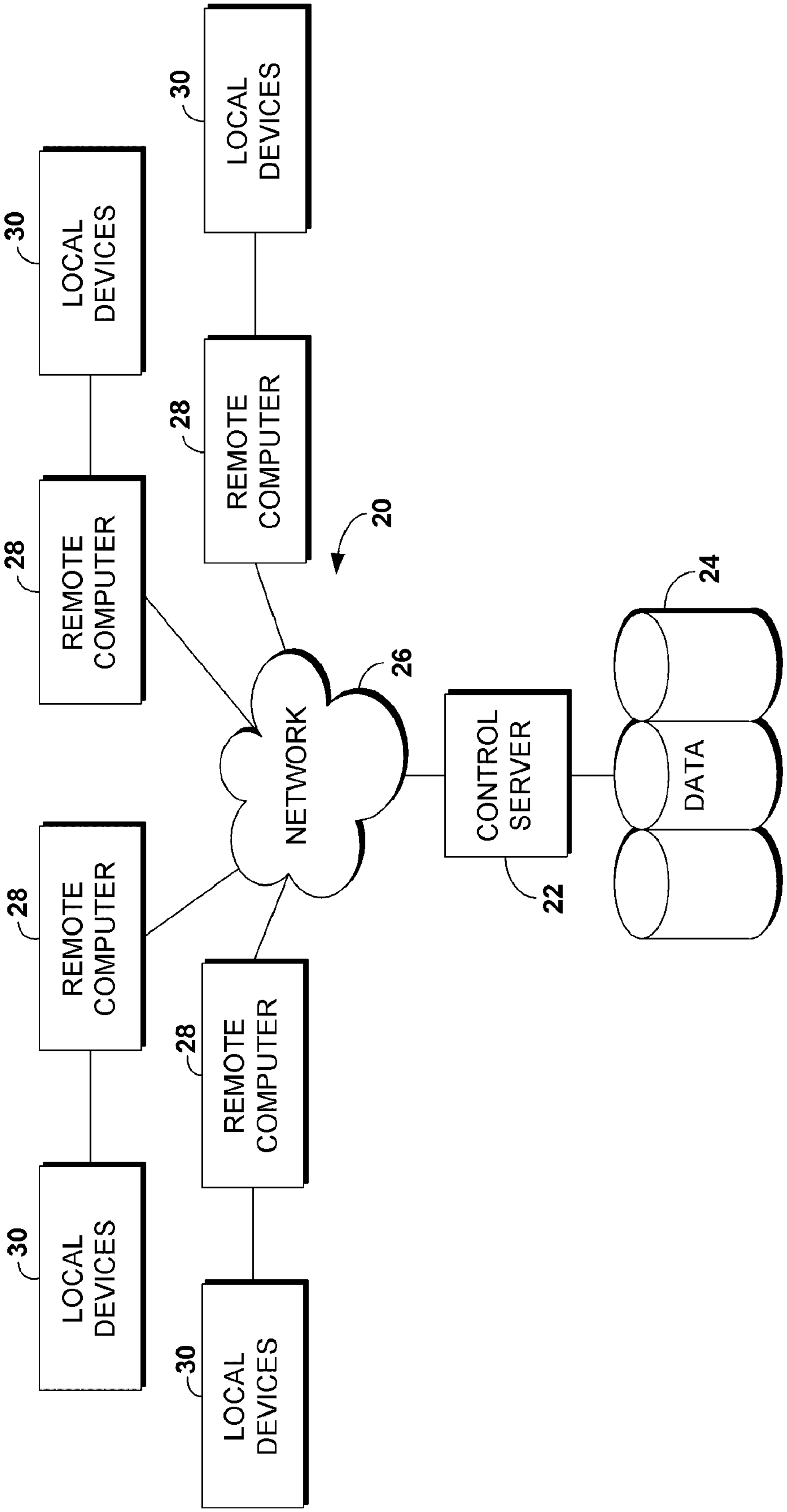
FIG. 1 is a block diagram of an exemplary computing environment suitable for use in implementing embodiments of the present invention.

Referring to the drawings in general, and initially to FIG. 1 in particular, an exemplary computing system environment, for instance, a medical information computing system environment, with which embodiments of the present invention may be implemented is illustrated and designated generally as reference numeral 20. It will be understood and appreciated by those of ordinary skill in the art that the illustrated medical information computing system environment 20 is merely an example of one suitable computing environment and is not intended to suggest any limitation as to the scope of use or functionality of the invention. Neither should the medical information computing system environment 20 be interpreted as having any dependency or requirement relating to any single component or combination of components illustrated therein.

The present invention may be operational with numerous other general purpose or special purpose computing system environments or configurations. Examples of well-known computing systems, environments, and/or configurations that may be suitable for use with the present invention include, by way of example only, personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention may be described in the general context of computer-executable instructions, such as program modules, being executed by a computer. Generally, program modules include, but are not limited to, routines, programs, objects, components, and data structures that perform particular tasks or implement particular abstract data types. The present invention may also be practiced in distributed computing environments where tasks are performed by remote processing devices that are linked through a communications network. In a distributed computing environment, program modules may be located in association with local and/or remote computer storage media including, by way of example only, memory storage devices.

With continued reference to FIG. 1, the exemplary medical information computing system environment 20 includes a general purpose computing device in the form of a control server 22. Components of the control server 22 may include, without limitation, a processing unit, internal system memory, and a suitable system bus for coupling various system components, including database cluster 24, with the control server 22. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The control server 22 typically includes therein, or has access to, a variety of computer-readable media, for instance, database cluster 24. Computer-readable media can be any available media that may be accessed by server 22, and includes volatile and nonvolatile media, as well as removable and non-removable media. By way of example, and not limitation, computer-readable media may include computer storage media and communication media. Computer storage media may include, without limitation, volatile and nonvolatile media, as well as removable and non-removable media implemented in any method or technology for storage of information, such as computer-readable instructions, data structures, program modules, or other data. In this regard, computer storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the control server 22.

Communication media typically embodies computer-readable instructions, data structures, program modules, or other data in a modulated data signal, such as a carrier wave or other transport mechanism, and may include any information delivery media. As used herein, the term “modulated data signal” refers to a signal that has one or more of its attributes set or changed in such a manner as to encode information in the signal. By way of example, and not limitation, communication media includes wired media such as a wired network or direct-wired connection, and wireless media such as acoustic, RF, infrared, and other wireless media. Combinations of any of the above also may be included within the scope of computer-readable media.

The computer storage media discussed above and illustrated in FIG. 1, including database cluster 24, provide storage of computer-readable instructions, data structures, program modules, and other data for the control server 22.

The control server 22 may operate in a computer network 26 using logical connections to one or more remote computers 28. Remote computers 28 may be located at a variety of locations in a medical or research environment, for example, but not limited to, clinical laboratories (e.g., molecular diagnostic laboratories), hospitals and other inpatient settings, veterinary environments, ambulatory settings, medical billing and financial offices, hospital administration settings, home health care environments, and clinicians’ offices. The remote computers 28 may also be physically located in non-traditional medical care environments so that the entire health care community may be capable of integration on the network. The remote computers 28 may be personal computers, servers, routers, network PCs, peer devices, other common network nodes, or the like, and may include some or all of the elements described above in relation to the control server 22. The devices can be personal digital assistants or other like devices. In addition, remote computer 28 may be in communication with local devices 30. Local devices 30 may include devices that monitor and record medical data. For example, a local device may include a Bedside Medical Device that can monitor and record physiological readings—such as, pulse rate, respiratory rate, oxygen saturation, body temperature, blood pressure, or the like.

Exemplary computer networks 26 may include, without limitation, local area networks (LANs) and/or wide area networks (WANs). Such networking environments are commonplace in offices, enterprise-wide computer networks, intranets, and the Internet. When utilized in a WAN networking environment, the control server 22 may include a modem or other means for establishing communications over the WAN, such as the Internet. In a networked environment, program modules or portions thereof may be stored in association with the control server 22, the database cluster 24, or any of the remote computers 28. For example, and not by way of limitation, various application programs may reside on the memory associated with any one or more of the remote computers 28. It will be appreciated by those of ordinary skill in the art that the network connections shown are exemplary and other means of establishing a communications link between the computers (e.g., control server 22 and remote computers 28) may be utilized.

In operation, a clinician may enter commands and information into the control server 22 or convey the commands and information to the control server 22 via one or more of the remote computers 28 through input devices, such as a keyboard, a pointing device (commonly referred to as a mouse), a trackball, or a touch pad. Other input devices may include, without limitation, microphones, satellite dishes, scanners, or the like. Commands and information may also be sent directly from a remote healthcare device to the control server 22. In addition to a monitor, the control server 22 and/or remote computers 28 may include other peripheral output devices, such as speakers and a printer.

Although many other internal components of the control server 22 and the remote computers 28 are not shown, those of ordinary skill in the art will appreciate that such components and their interconnection are well known. Accordingly, additional details concerning the internal construction of the control server 22 and the remote computers 28 are not further disclosed herein.

Although methods and systems of embodiments of the present invention are described as being implemented in a WINDOWS operating system, operating in conjunction with an Internet-based system, one of ordinary skill in the art will recognize that the described methods and systems can be implemented in any system supporting the receipt and processing of medical documentation, particularly, presenting medical documentation sets and receiving attributes for medical data fields associated with medical documentation sets. As contemplated by the language above, the methods and systems of embodiments of the present invention may also be implemented on a stand-alone desktop, personal computer, or any other computing device used in a healthcare environment or any of a number of other locations.

As previously mentioned, embodiments of the present invention relate to methods, systems, and computer-readable media for use in, e.g., a healthcare environment, for generating and/or managing one or more sets of medical documentation. For simplicity, the particular user will often be referred to herein as a clinician. Clinicians may include, but are not limited to, a treating physician or physicians, specialists such as surgeons, radiologists, cardiologists, and oncologists, emergency medical technicians, physicians' assistants, nurse practitioners, nurses, nurses' aides, pharmacists, dieticians, microbiologists, laboratory experts, laboratory technologists, genetic counselors, researchers, veterinarians, students, and the like. In general, it will be understood that the particular user may be any healthcare professional, physician, or other provider, as described above.

As used herein, the terms "individual," "person," and "patient" are used interchangeably herein and are not meant to limit the nature of the referenced individual in any way. Rather, the methods and systems described herein are equally applicable, for instance, in a veterinary setting. Further, use herein of the term "patient" is not meant to imply any particular relationship between the individual in question and those generating medical templates, generating medical documentation sets, managing medical documentation sets, and the like.

As used herein, the phrase "medical documentation set" refers to a set or group of associated medical documentation that is presented in an electronic form and may be used to document medical data. The medical documentation sets may include a single medical documentation element or a plurality of medical documentation elements depending on the medical event being documented. In one embodiment, a medical documentation set may include, among other things, fields for a medical label, medical label elements, medical documentation elements, medical data fields, or a combination thereof. Specific examples of medical documentation sets and medical documentation elements will be discussed in more detail below.

A "medical documentation element," as used herein, identifies a medical aspect for which corresponding medical data may be documented. For example, a medical documentation element comprising "cough" indicates that medical data providing an indication of sputum characteristics may be documented for a "productive" cough. In some embodiments, a medical documentation element may be positioned adjacent to or near one or more medical data fields that allow for documenting medical data. In particular, a "medical data field," as used herein, refers to an area in which an attribute of medical data may be entered for a corresponding medical document element. "Medical data," as used herein, refers to any data associated with a medical documentation element that is documented in a medical data field within a medical documentation set. For example, assume a medical documentation element comprising "cough" is presented within a medical documentation set. Medical data may include any data that indicates the sputum characteristics for a productive cough, such as, for example, "small", "clear", or "thin." This medical data may be documented by a clinician at the time of service or care.

One skilled in the art will appreciate that a medical documentation set can be generated based on a medical template. A "medical template," as used herein, refers to a set of elements that define a unique format intended to be replicated for documenting medical data. A medical template may include one or more medical label elements that are used to define a medical label, medical documentation elements that identify medical data, and/or medical data fields that may, upon replication, receive medical data input within a medical documentation set. Upon the generation of a medical template, the medical template can be replicated, or otherwise used, to generate a medical documentation set having a form similar to the medical template such that a clinician can document medical data.

Figure 2:
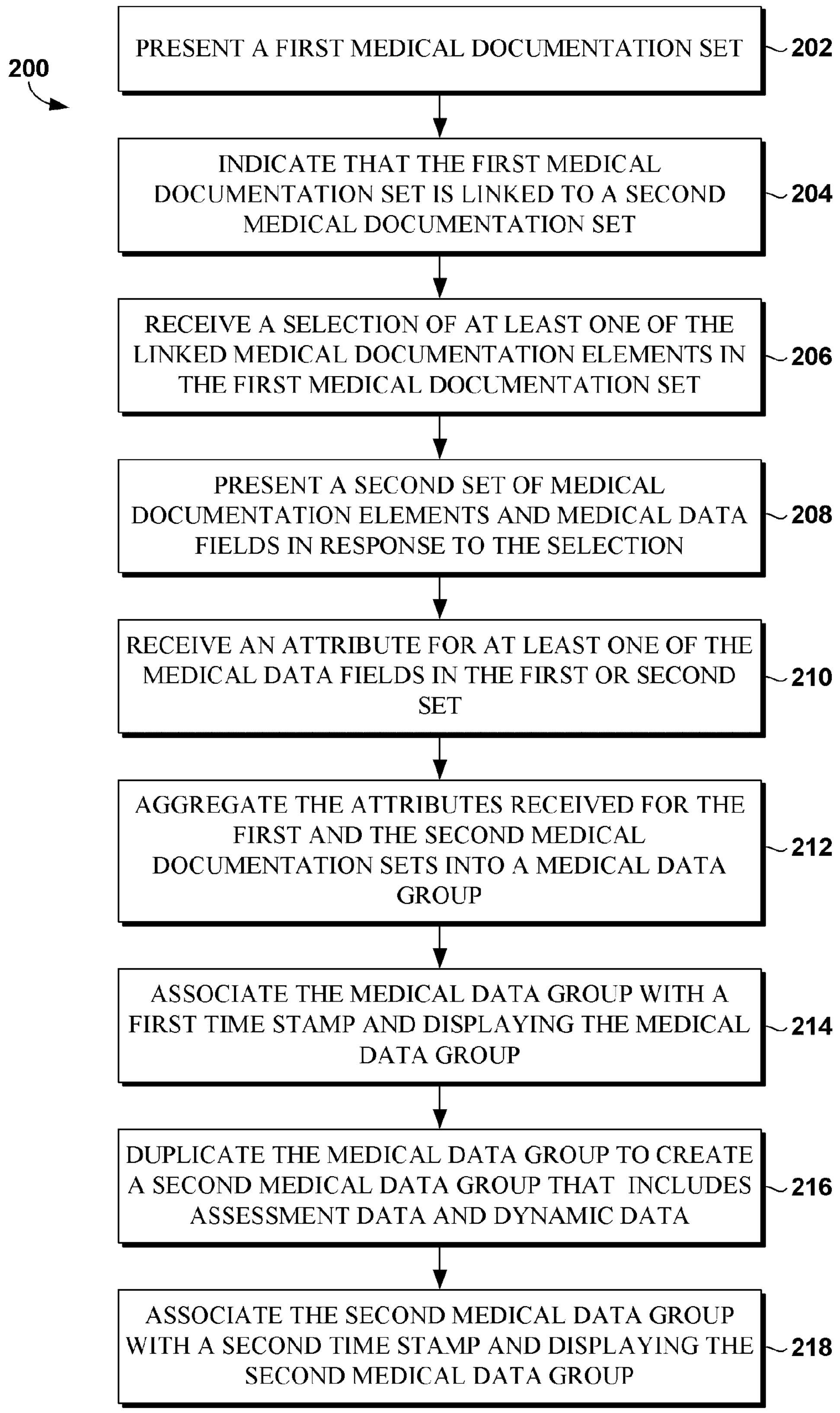
FIG. 2 is a flow diagram showing a method for guiding a clinician to complete medical documentation, in accordance with an embodiment of the present invention.
Figure 7:
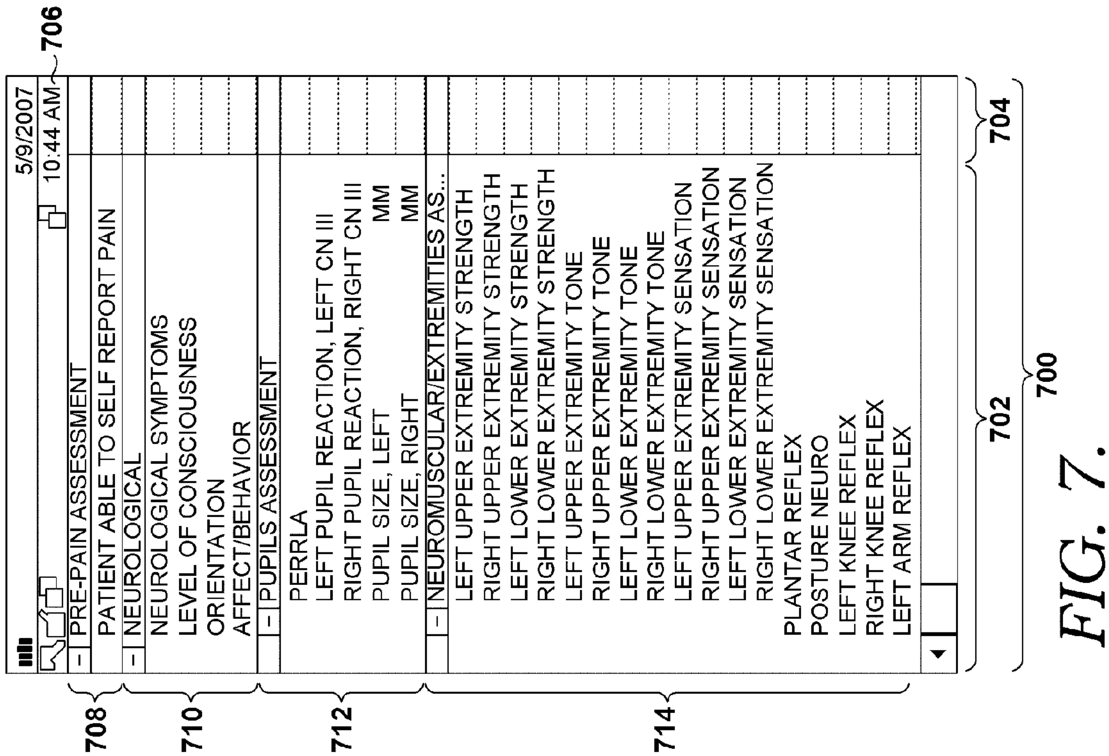
FIG. 7 is an illustrative screen display of an exemplary user interface for viewing a first medical documentation set, in accordance with an embodiment of the present invention.

FIG. 2 illustrates a method 200 in accordance with one embodiment of the present invention that guides a clinician to complete medical documentation. At 202, the method includes presenting a first medical documentation set to a clinician. The first medical documentation set includes a first set of medical documentation elements and a first set of medical data fields to indicate a medical aspect for which medical data is to be documented. FIGS. 3 and 7 illustrate two possible examples of presenting a first medical documentation set to a clinician. FIGS. 3 and 7 will be discussed in more detail below.

Figure 4:
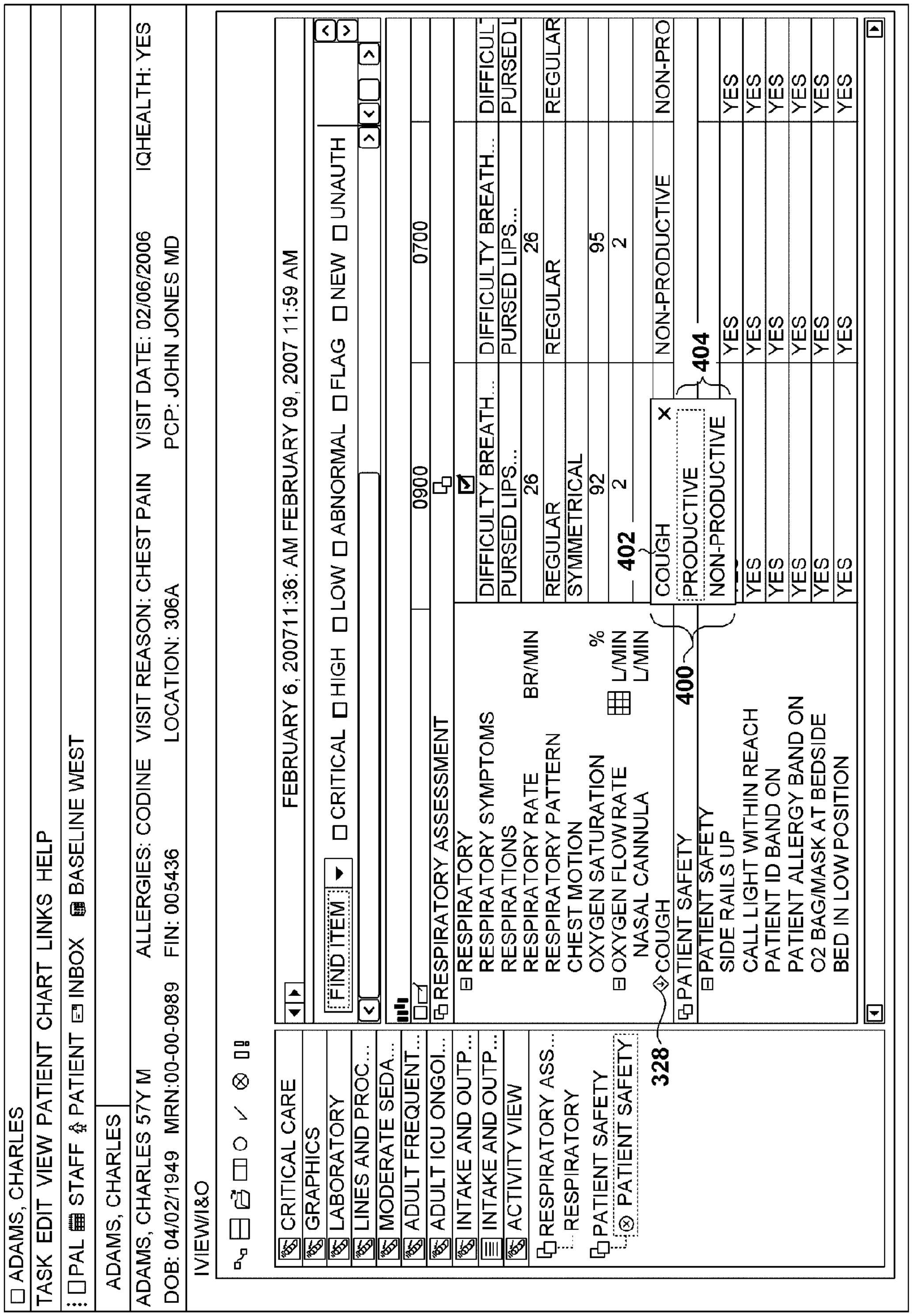
FIG. 4 is an illustrative screen display of an exemplary user interface, in accordance with an embodiment of the present invention, that may be utilized to trigger a link to a second medical documentation set.

At 204, the method 200 indicates that at least one of the medical documentation elements in the first set is linked to a second medical documentation set. The second medical documentation set includes a second set of medical documentation elements and a second set of medical data fields to indicate a medical aspect for which medical data is to be documented. FIG. 4 illustrates one possible example of indicating that at least one of the medical documentation elements in the first set is linked to a second medical documentation set. This indication may include presenting an icon in association with at least one of the medical documentation elements presented in the first set or implementing a distinguishable font to display at least one of the medical documentation elements presented in the first set. FIG. 4 will be discussed in more detail below.

Optionally, method 200 may include indicating that at least one of the medical documentation elements in the second medical document set is linked to a third medical documentation set. The third medical documentation set may include a third set of medical documentation elements and a third set of medical data fields to indicate a medical aspect for which medical data is to be documented.

At 206, the method 200 receives a selection of at least one of the linked medical documentation elements in the first set. This may include receiving an attribute for one of the medical data fields in the first set. FIG. 4 illustrates one possible example of receiving an attribute for one of the medical data fields in the first set. FIG. 4 will be discussed in more detail below.

Figure 5:
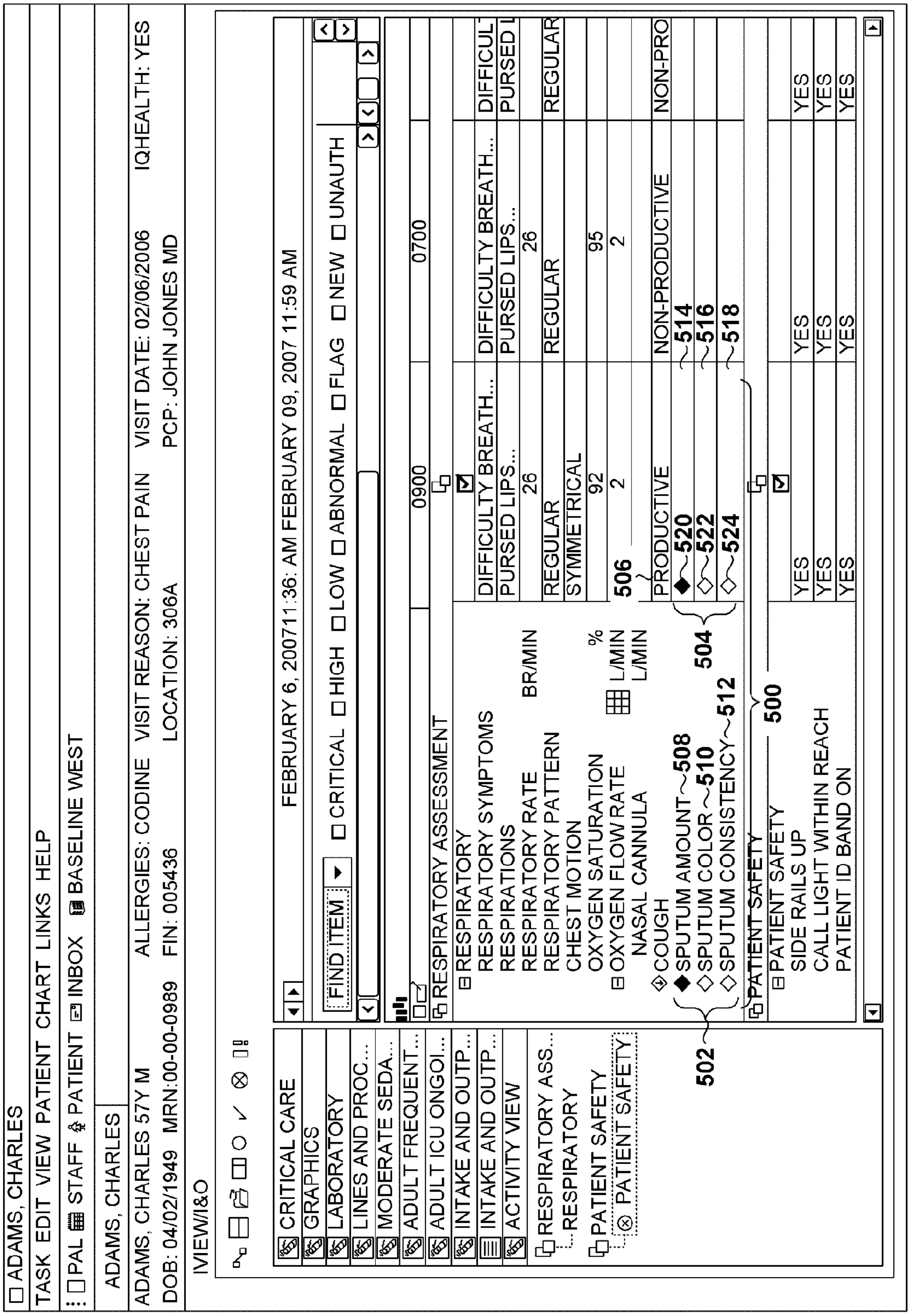
FIG. 5 is an illustrative screen display of an exemplary user interface, in accordance with an embodiment of the present invention, that may be utilized for documenting a first and second medical documentation set.

At 208, the method 200 presents the second set of medical documentation elements and medical data fields in response to the selection. FIG. 5 illustrates one possible example of presenting the second set of medical documentation elements and medical data fields in response to the selection. The second medical documentation set is exemplary of conditional logic that guides the clinician in completing the medical documentation. In some embodiments, the conditional logic presents the second medical documentation set when any attribute is provided for a particular medical documentation element. In other embodiments, the second medical documentation set is provided only if a predetermined attribute is received in a medical data field for a particular medical documentation element. For example, if the attribute "productive" was selected or received in the data field associated with the documentation element "cough," then the second medical documentation set might be presented. In contrast, if the attribute "nonproductive" was selected or received in the data field associated with the documentation element "cough," then a second medical documentation set might not be presented at all. Thus, conditional logic helps to guide the clinician in completing the medical documentation by presenting the most relevant documentation sets and elements relating to the medical aspect to be documented. This provides presenting the medical documentation sets in a concise form making them easier to read and interface.

Figure 12:
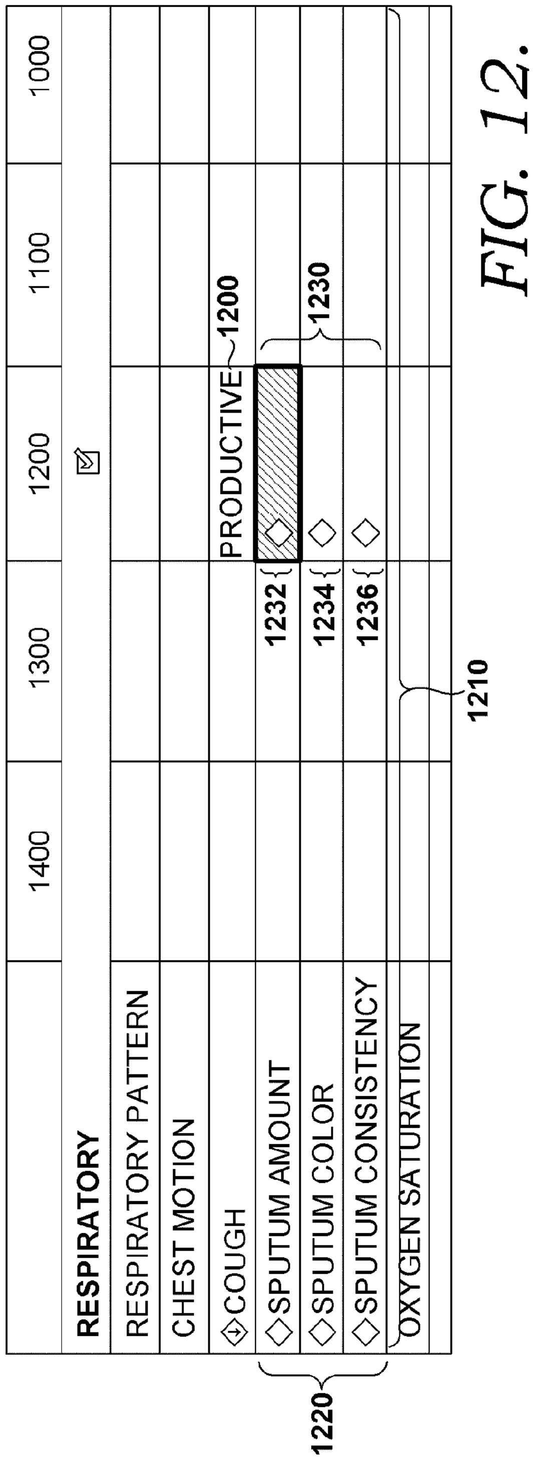
FIG. 12 is an illustrative screen display of an exemplary user interface, in accordance with an embodiment of the present invention, that may be utilized for documenting a first and second medical documentation set.

At 210, the method 200 receives an attribute for at least one of the medical data fields in the first or second set. The method may indicate that an attribute is required for at least one of the medical data fields in the first set, the second set, or both sets. This indication may include implementing an icon, a font, a color indicator, an audio signal, or combination thereof to distinguish the required medical data field from the other medical data fields. FIG. 12 illustrates one possible example of indicating that an attribute is required for at least one of the medical data fields in the first set, the second set, or both sets, and will be discussed in more detail below. In addition, receiving an attribute may include medical data documented at a point of care in association with medical care provided to a patient. FIG. 12 will be discussed in more detail below.

Figure 6:
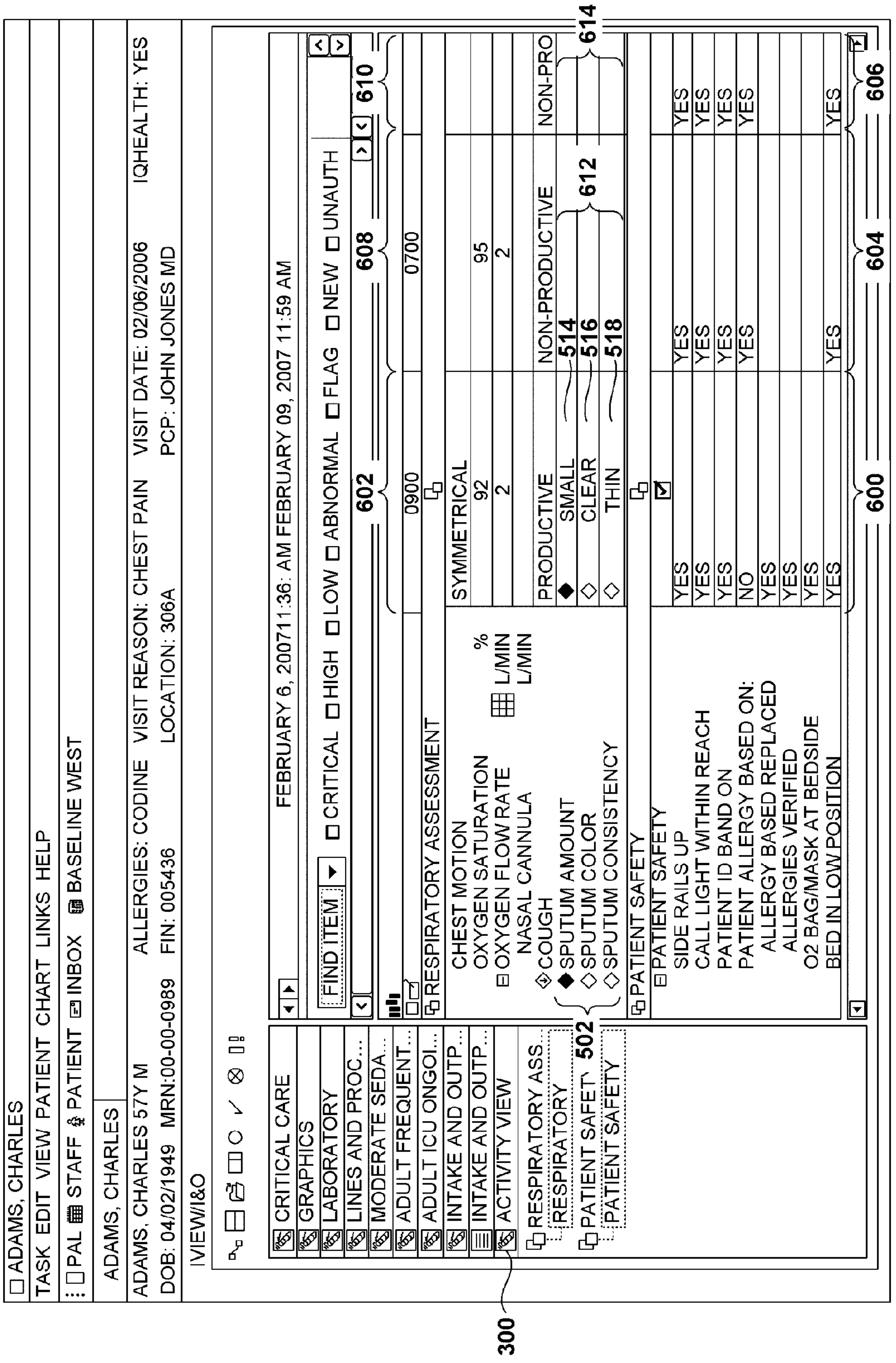
FIG. 6 is an illustrative screen display of an exemplary user interface for viewing an aggregated medical data group, in accordance with an embodiment of the present invention.

At 212, the method 200 aggregates the attributes received for the first and the second medical documentation sets into a medical data group. At 214, the method 200 may associate the medical data group with a first time stamp and present the medical data group to a clinician. FIG. 6 illustrates one possible example of aggregating the attributes received, associating the medical data group with a first time stamp, and presenting the medical data group to a clinician. FIG. 6 will be discussed in more detail below.

In one embodiment, at 216, the method 200 may also include duplicating the medical data group to create a second medical data group. This includes duplicating assessment data and dynamic data. As discussed, dynamic data may include physiological readings—such as, pulse rate, respiratory rate, oxygen saturation, body temperature, blood pressure, or the like that may be entered by a clinician or obtained from a Bedside Medical Device. Assessment data may include any other data that is used to document medical aspects. For example, it may include an observation or an assessment of the dynamic data or any other medical observations or recording. Duplicating the dynamic data may include updating the dynamic data in the second medical data group via a medical device interface. At 218, the method 200 includes associating the second medical data group with a second time stamp and displaying the second medical data group. FIGS. 15-16 illustrate possible examples of aggregating the attributes received, associating the medical data group with a second time stamp, and presenting the medical data group to a user. FIGS. 15-16 will be discussed in more detail below.

Figure 18:
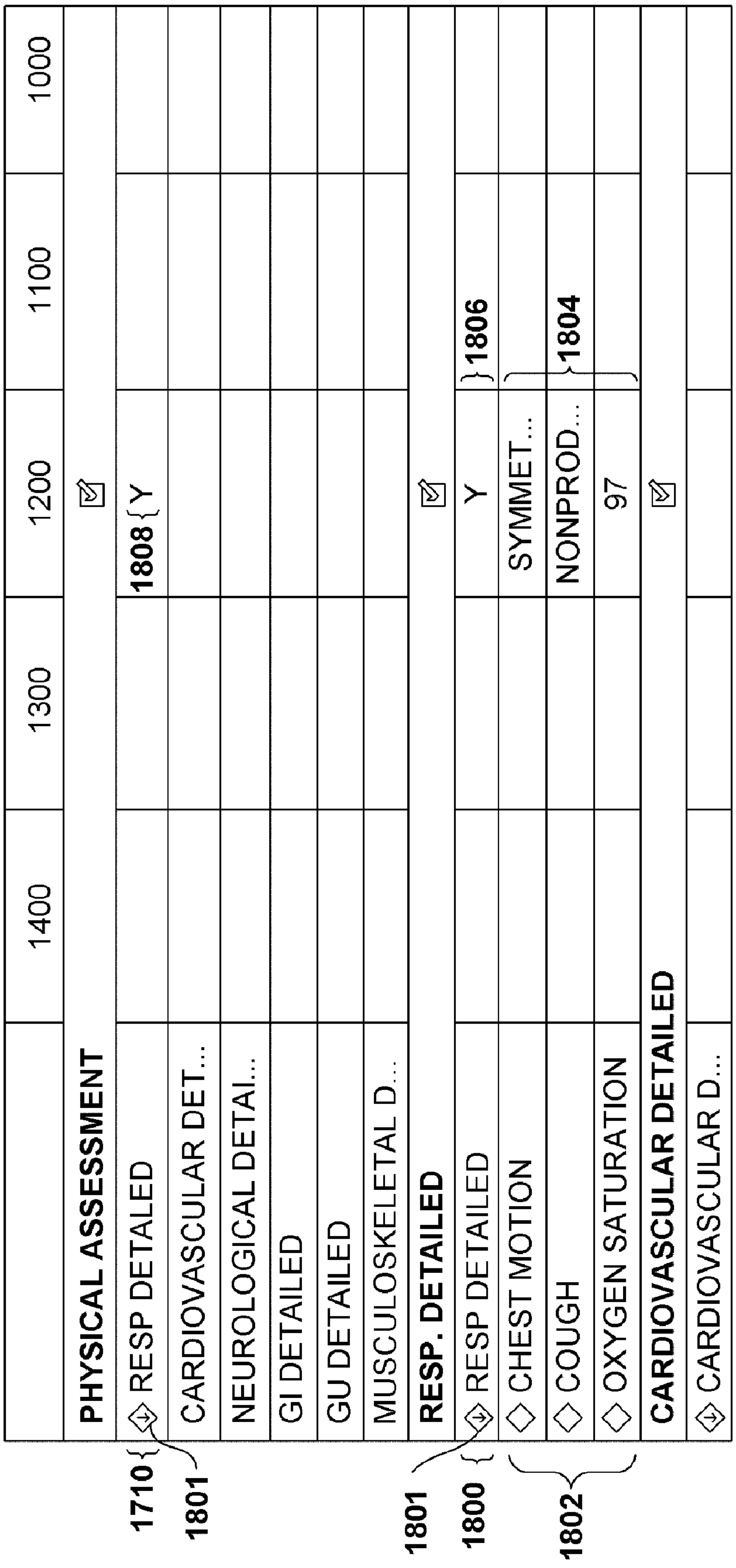
FIG. 18 is an illustrative screen display of an exemplary user interface for viewing attributes related to a medical documentation element in two dynamic sections, in accordance with an embodiment of the present invention.
Figure 26:
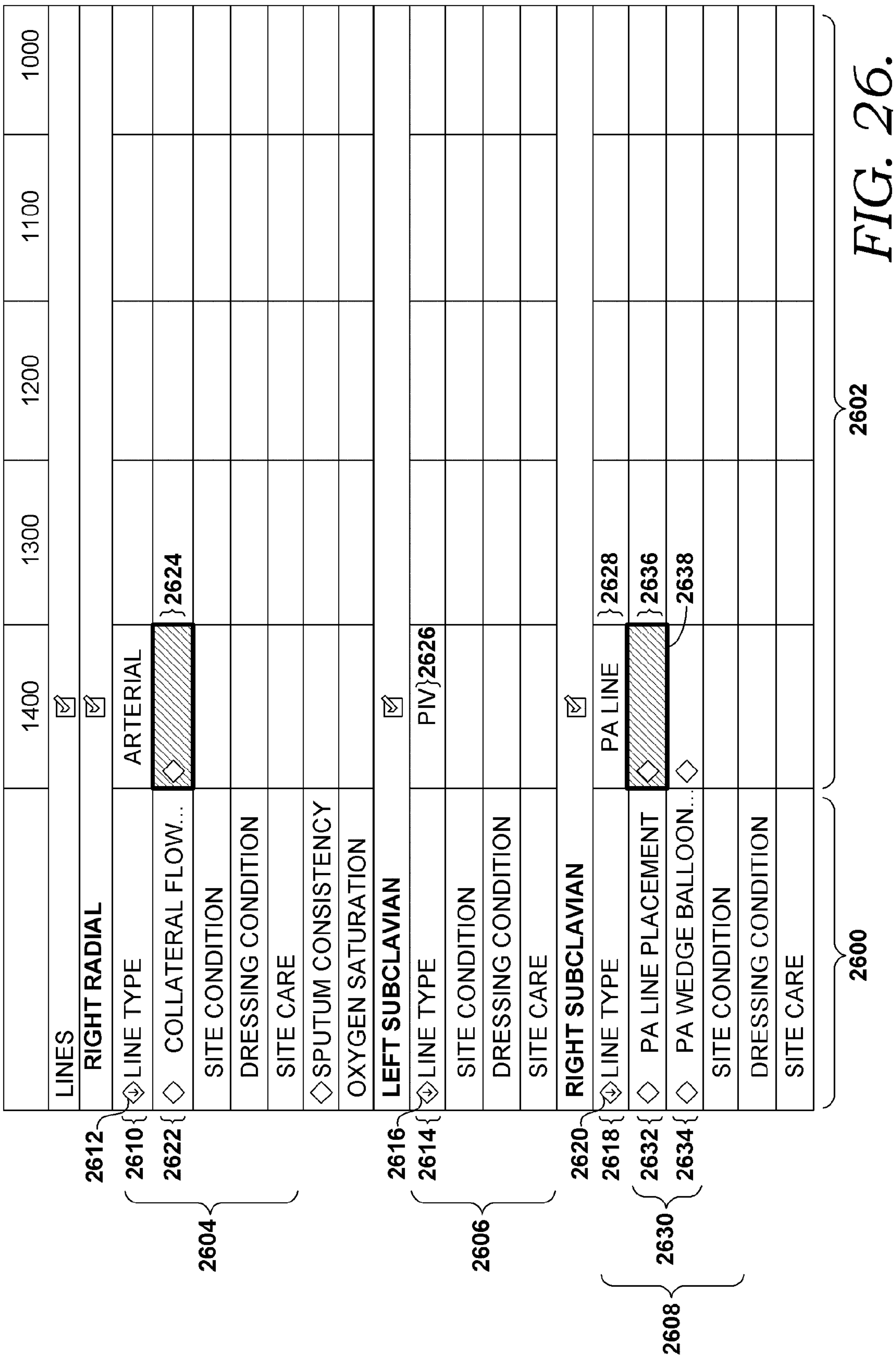
FIG. 26 is an illustrative screen display of an exemplary user interface, in accordance with an embodiment of the present invention, that may be utilized for documenting a plurality of documentation elements in a plurality of dynamic sections.

In some embodiments, the first medical document set may also include multiple sections. A section may include a grouping of medical documentation elements and associated medical data fields relating to a particular medical aspect requiring documentation. Each section may include elements that are linked or cross-referenced to another. FIG. 18 illustrates one possible example of a first medical document set that includes at least two sections having a linked documentation element. Specifically, the figure illustrates three sections labeled "physical assessment", "resp. detailed", and "cardiovascular detailed." The "resp detailed" element 1710, 1801 is presented and is cross-referenced in both the "physical assessment" and "resp. detailed" section. Alternatively, the first medical documentation set may include a plurality of sections with each section having independent elements that are not cross referenced but instead are linked to separate second medical documentation sets. FIG. 26 illustrates one possible example of first medical documentation set that includes a plurality of sections with each section having a link to a separate second medical documentation set as will be discussed in more detail below. FIG. 26 will be discussed in more detail below.

In one embodiment, at 218, the method 200 may include receiving a modification to at least one of the medical data fields in the second medical data group and indicating a modification to at least one of the medical data fields in the second medical data group. FIG. 20 illustrates one possible example of receiving and indicating a modification to at least one of the medical data fields in the second medical data groups. FIG. 20 will be discussed in more detail below.

Turning now to FIGS. 3-26, a series of exemplary conditional logic screen displays and user interfaces for facilitating the completion of medical documentation is provided. It will be understood and appreciated by those of ordinary skill in the art that the series of conditional logic screen displays presented in FIGS. 3-26 is exemplary in nature and is not intended to limit the scope of the invention in any way. The user interfaces may be any electronic display where clinicians have access to generate a medical documentation set. For example, the user interfaces may be displayed on remote computers 28 of FIG. 1. The clinician may then interact with the user interface using well known input components—such as, for example, a mouse, a joystick, a stylus, a touch screen, a keyboard, or the like. In addition, remote computers 28 may communicate with one another via network 26, as well as, communicate with local devices 30. Local devices may include devices that monitor and record medical data. As discussed, a local device may include a Bedside Medical Device that can monitor and record physiological readings—such as, pulse rate, respiratory rate, oxygen saturation, body temperature, blood pressure, or the like.

By way of example only, assume the text "productive" is identified as a predetermined attribute. Assume further that a clinician enters the text "productive" in a medical data field that is associated with a medical documentation element "cough." The documentation receiving component might determine that the predetermined attribute "productive"

exists within a medical data field. As such, the documentation receiving component may provide another medical documentation element titled "sputum amount" and one or more corresponding medical data fields within the initial medical documentation set based on conditional logic.

By way of illustration only, the exemplary displays of FIGS. 3-6 illustrate documentation views of conditional logic screens displayed to a clinician in charting a medical documentation set within a software application. The software application may include, for example, Power Chart®, Power Chart Office®, and other Cerner Millennium® applications marketed by the Cerner Corporation of Kansas City, Mo. A documentation view refers to a view having specific information within the software application, such as, for example, Interactive View, Intake and Output View, RN View, or Activity View within the PowerChart® application.

Specifically, FIG. 3 illustrates an exemplary display in the "Activity View" 300 of Cerner's Power Chart® application. In this example, the display is presented to a clinician for documenting the medical records 302 of a hypothetical patient named "Charles Adams." As illustrated, the "Activity View" window 300 provides a plurality of medical documentation sets 304. The medical documentation sets 304 may include a single medical documentation element or a plurality of medical documentation elements 306 depending on the medical event being documented. For example, medical documentation elements may include "respiratory" elements 310, "oxygen flow rate" elements 312, "cough" elements 314, or "patient safety" elements 316. These medical documentation elements 306 may be associated with a single medical data field or a plurality of medical data fields 308. In sum, the medical documentation elements 306 and the medical data field 308 indicate a medical aspect for which medical data is to be documented.

Each of theses medical documentation elements may further include subelements as illustrated in FIG. 3. The subelements may be displayed as individual elements or may be presented as a group. For example, respiratory element 310 may include subelement group 318 that includes "respiratory symptoms", "respirations", "respiratory rate", "respiratory pattern", "chest motion", and "oxygen saturation." A subelement may be considered an individual medical documentation element even though it is included in a subelement group. Thus, the designation of subelement is used as an indicator of a possible parent-child relationship between two documentation elements.

Each of the medical documentation elements 306 and subelements may be associated with medical data fields 308. Specifically, the medical data fields 308 provide an area in the "Activity View" 300 for receiving an attribute related to a medical aspect for which medical data is to be documented. It will be understood and appreciated by those of ordinary skill in the art that the medical data fields 308 may include a number of different types of attributes. For example, they may include a specific descriptor, such as, "Difficulty breath . . . " 320 entered into the data field associated with the "Respiratory Symptoms" element; a numeric value, such as, "26" 322 entered into the data field associated with the "Respiratory Rate" element; or a general descriptor, such as, "regular" 324 entered into the data field associated with the "Respiratory Pattern" element. The attributes received for the individual medical data fields may be grouped together as a medical data group and associated with a time stamp. For example, medical data group 326 illustrated in FIG. 3 is associated with time stamp 327 which has a value of "0900." Grouping the attributes and associating them with a specific time stamp provides a way to display the data group in a chronological format.

Each of the medical documentation sets 310, 312, 314, 316 may be linked to a second medical documentation set that is not initially displayed or presented to the clinician. One possible reason for "hiding" this second documentation set is to reduce the number of medical data fields that are initially presented to the clinician. This avoids cluttering the display and increases the readability of the user interface. One way of reducing the clutter is to display the second documentation set only if one of the documentation elements in the first set is selected. Thus, the second medical documentation set can remain hidden from the display until it is "triggered." In so doing, the user interface guides the clinician in documenting the medical aspects for each medical documentation elements. Reducing clutter and guiding the clinician in documenting the medical aspects are a few possible benefits provided by utilizing embodiments of the invention.

Even though the second medical documentation set may be hidden from the clinician, the user interface may provide an indicator that a second documentation set is associated or linked with one of the displayed medical documentation elements. For example, in FIG. 3, the "cough" element 314 is associated with icon 328 to indicate that a second medical documentation set may be displayed if the "cough" element is selected or triggered. There may be a number ways to indicate to a clinician that such a link exists. For example, the use of bold text, a color indicator, an audio signal, other distinguishing font, or any other differentiating feature may be used to indicate that the first medical documentation set is linked to a second medical documentation set. For example, bold text may be useful in the scenario where the clinician is color blind or the display is limited to a monochrome format.

Similar to indicating a link to a second medical documentation set, there are a number of ways to trigger the display or presentation of the second medical documentation set. For example, the second medical documentation set may be presented when the clinician selects icon 328 or enters an attribute in the related medical data field 330. Another trigger may be when an attribute falls above or below a predetermined threshold. For example, a trigger may occur if the respiratory rate exceeded or dropped below a predetermined value. By way of illustration only, FIG. 4 illustrates an exemplary conditional logic dialog box 400 that appears when the clinician selects data field 402. The dialog box 400 includes a list 404 that displays two attributes that are linked to a second or other medical documentation set. Specifically, the list 404 includes "productive" and "non-productive" attributes that may be presented to the clinician. Each of these attributes may be linked to the same second medical documentation set or a different documentation set depending on the medical documentation element to be documented.

By way of illustration only, FIG. 5 illustrates a conditional logic example of a second medical documentation set 500 that is presented to a clinician upon selection of the "productive" attribute displayed in FIG. 4. Similar to the first medical documentation set 304, the second medical documentation set 500 may include a second set of medical documentation elements 502 and medical data fields 504. Again, the medical documentation elements 502 and the medical data field 504 may indicate a medical aspect for which medical data is to be documented. For example, the second set of medical documentation elements illustrated in this example include "sputum amount" 508, "sputum color" 510, and "sputum consistency" 512.

The second set of medical data fields 504 associated with the second set of medical documentation elements 502 are illustrated by the three medical data fields 514, 516, 518. These data field may include an indication that an attribute is either required or is optional for the referenced data field. In this example, the conditional logic user interface indicates that an attribute is required for the "sputum amount" data field 514 as indicated by the completely shaded diamond icon 520. In contrast, the unshaded diamond icons 522 and 524 for the "sputum color" 516 and "sputum consistency" 518 data fields indicate that an attribute is optional for these data fields. Similar to indicating a link to a second medical documentation set, there may be a number of ways to indicate to a clinician that a data field is either required or optional. For example, the use of bold text, any other distinguishing font, a color indicator, an audio signal, or any other differentiating feature may be used to indicate that an attribute is either required or optional for the data field. In addition, a "required" data field does not necessarily mean that the clinician has to enter an attribute. For example, the method or system may provide a "Not Done" option for required data fields where the clinician has not entered an attribute. Thus, the term "required," as used in referring to data field, is used to establish a hierarchal relationship between the medical data fields presented to a clinician. Embodiments of the present may even include different hierarchal levels within the "required" label.

By way of illustration only, FIG. 6 illustrates a conditional logic user interface after the clinician has entered attributes for the required data field 514 and optional data fields 516, 518. Specifically, the interface displays "small" for required data field 514, "clear" for optional data field 516, and "thin" for optional data field 518. The figure further illustrates that these attributes may be aggregated into a medical data group 600. The medical data group 600 may be associated with a specific time stamp. In this example, the medical data group 600 is associated with time stamp 602 having "0900" description. FIG. 6 also illustrates that there may be a plurality of aggregated medical data groups associated with a plurality of time stamps. For example, medical data group 604 may associated with time stamp 608 and medical data group 606 may be associated with time stamp 610. In addition, FIG. 6 illustrates that once populated with attributes, second set of medical data fields 612, 614 may be displayed in the other medical data groups 604, 606. This does not mean that these fields now require an attribute, but rather illustrate which document set contain medical data elements for the second medical documentation set and which ones do not. This provides the ability to view previously documented results in the context of the current documentation. It also provides initial guidance on which medical documentation elements were documented in the past and may be required when documenting similar medical events in the future.

By way of illustration only, the exemplary displays of FIGS. 7-10 illustrate views of conditional logic screens displayed to a clinician in generating a medical documentation set 700 including documentation elements that are different from the ones displayed in FIGS. 3-6. Specifically, FIG. 7 illustrates one possible conditional logic example of a first set of medical documentation elements 702 associated with a first set of medical data fields 704. As before, medical data fields 704 indicate a medical aspect for which medical data is to be documented. The medical documentation elements 702 and medical data fields 704 form the first medical documentation set 700 that may be associated with a time stamp 706. Referring to FIG. 3, the medical documentation set 700 may be presented in a similar manner as the medical documentation set 304 in "Activity View" 300.

As illustrated, the first medical documentation set 700 may include a plurality of medical documentation elements. For example, the medical documentation elements may include "pre-pain assessment" 708, "neurological" 710, "pupils assessment" 712, and "neuromuscular/extremity as . . . " 714. Each of these medical documentation elements may include subelements as illustrated in FIG. 7. As before, first medical documentation set 700 may be linked to a second medical documentation set that is presented when a clinician triggers a link to the second medical documentation set. In the illustrated example, this link may be triggered when the clinician enters an attribute in one of the medical data fields 704.

Figure 8:
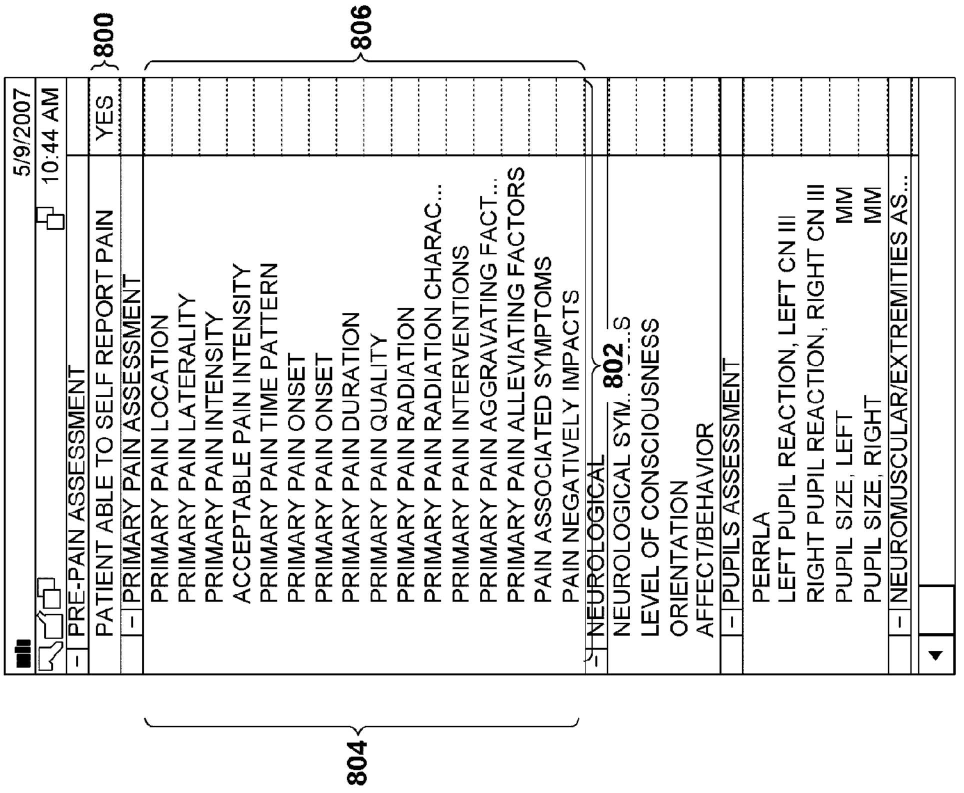
FIG. 8 is an illustrative screen display of an exemplary user interface, in accordance with an embodiment of the present invention, that may be utilized to trigger a link to a second medical documentation set.

By way of illustration only, FIG. 8 illustrates the resulting conditional logic user interface when a clinician enters "yes" for the attribute in the first medical data field 800 in the "pre-pain assessment" element group 708. Upon entering an attribute in the first medical data field 800, a second medical documentation set 802 is presented to the clinician. The second medical documentation set may include a second set of medical documentation elements 804 and a second set of medical data fields 806. Again, the medical data fields 806 indicate a medical aspect for which medical data may need to be documented.

Figure 9:
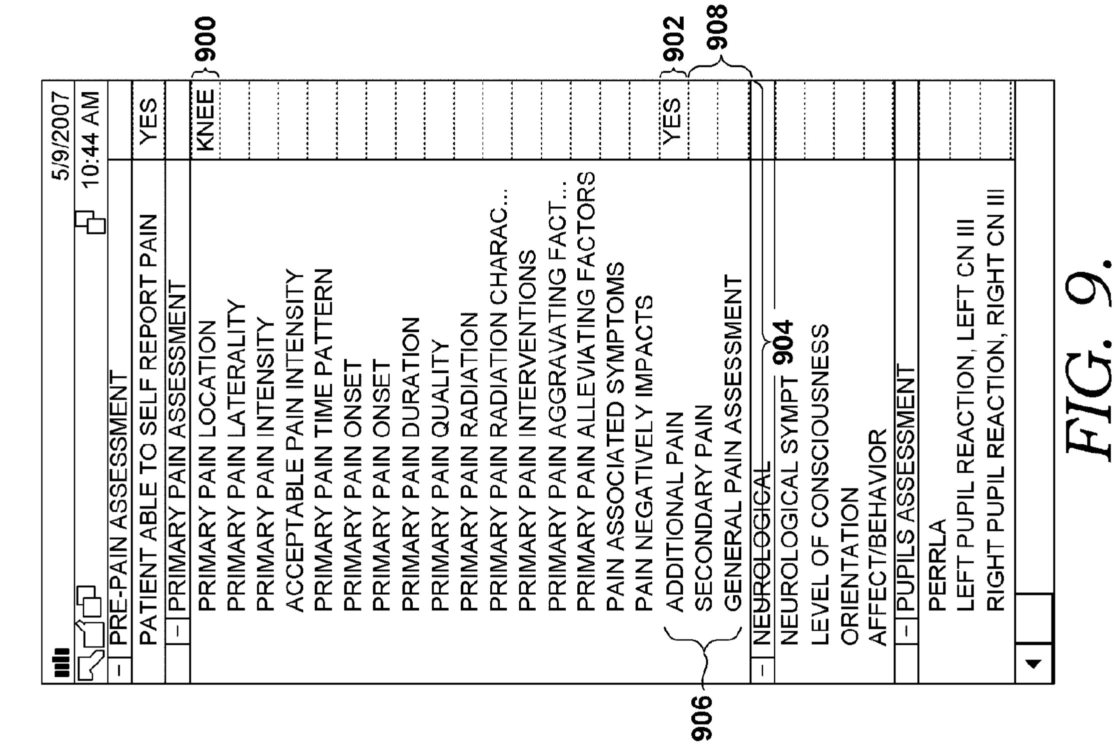
FIG. 9 is an illustrative screen display of an exemplary user interface, in accordance with an embodiment of the present invention, that may be utilized to trigger a link to a third medical documentation set.

By way of illustration only, FIG. 9 illustrates the resulting conditional logic user interface when a clinician enters "knee" for the attribute in the first medical data field 900 of the "primary pain assessment" element group 804. Upon entering an attribute in the medical data field 900, a third medical documentation set 904 is presented to the clinician. The third medical documentation set may include a third set of medical documentation elements 906 and a third set of medical data fields 908. Again, the medical data fields 908 indicate a medical aspect for which medical data may need to be documented. In the examples illustrated in FIGS. 7-9, the medical data fields were generally illustrated as optional, however, any of these data fields or documentation could be indicated as required and presented in a similar manner as illustrated in FIGS. 3-7.

Figure 10:
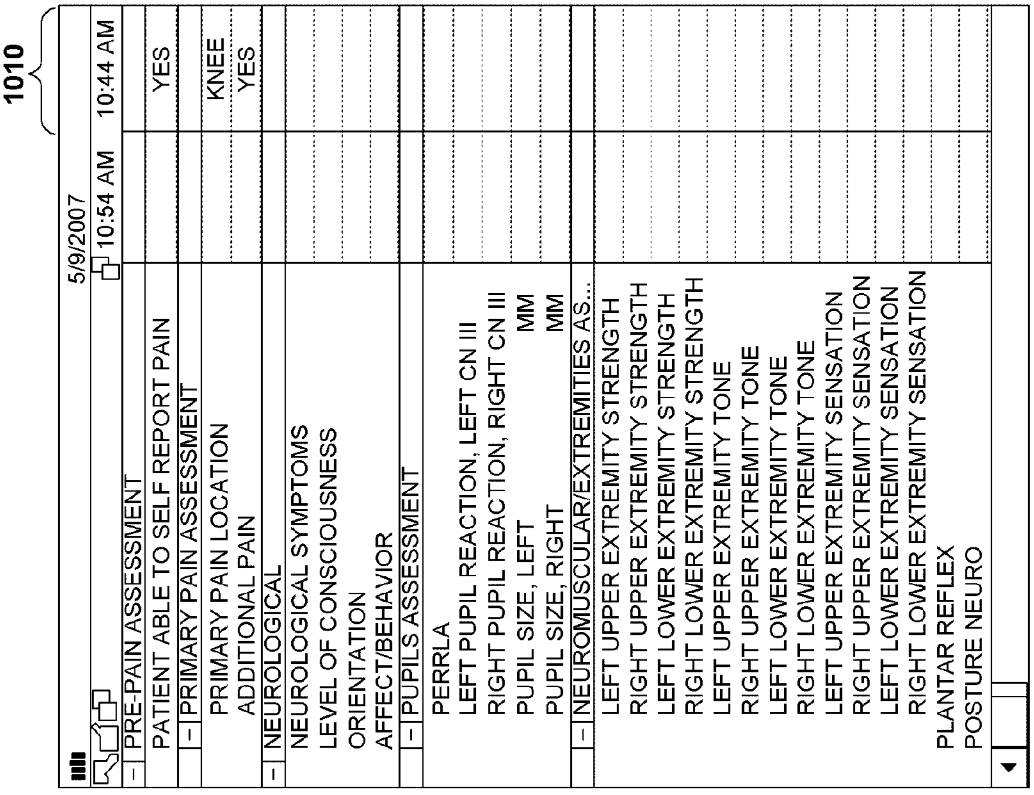
FIG. 10 is an illustrative screen display of an exemplary user interface for viewing an aggregated medical data group, in accordance with an embodiment of the present invention.

By way of illustration only, FIG. 10 illustrates the resulting conditional logic user interface once the clinician has completed entering data in the medical data fields of FIGS. 7-9. In the figure, the user interface displays an aggregated or condensed medical data group 1000. As illustrated, the empty data fields associated with second medical data elements 804 and third medical data elements 906 are not displayed once the attributes are aggregated or combined into medical data group 1000. As before, medical data group 1000 may be associated with a time stamp 1010.

Figure 11:
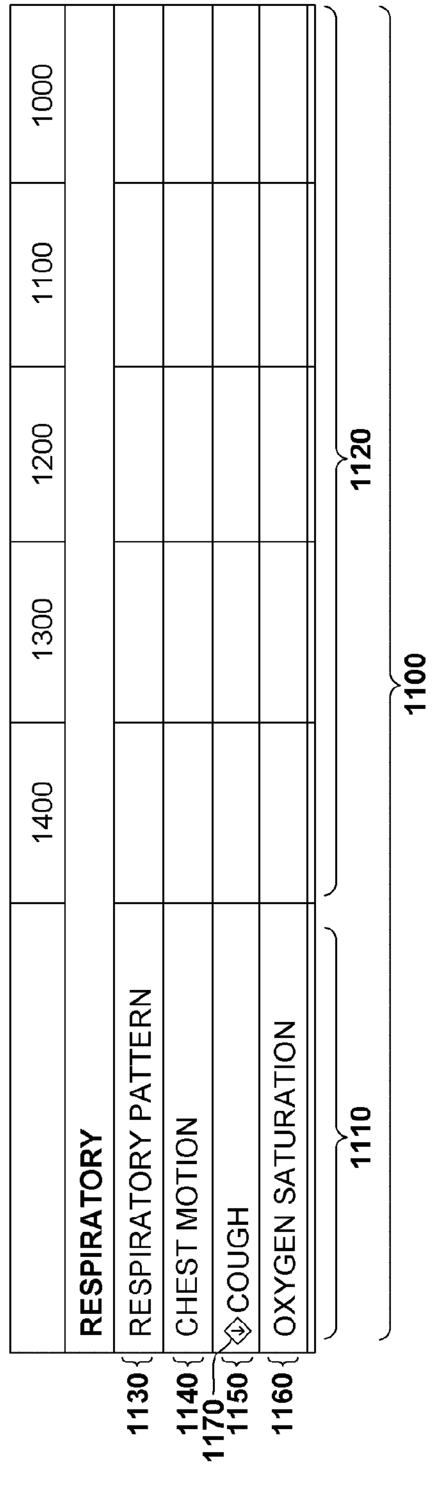
FIG. 11 is an illustrative screen display of an exemplary user interface for viewing a first medical documentation set, in accordance with an embodiment of the present invention.

By way of illustration only, FIGS. 11-14 illustrate another conditional logic example of the user interface included in some embodiments of the inventions. Specifically, FIG. 11 illustrates a medical documentation set 1100 having a first set of medical documentation elements 1110 and a first set of medical data fields 1120. As before, there may be plurality of medical documentation elements in the first medical documentation set 1100. For example, FIG. 11 illustrates medical documentation elements "respiratory pattern" 1130, "chest motion" 1140, "cough" 1150, and "oxygen saturation" 1160. Likewise, icon 1170 indicates that medical documentation element "cough" 1150 is associated or linked to a second medical documentation set.

By way of illustration only, FIG. 12 illustrates the resulting conditional logic user interface when a clinician enters an attribute in the "cough" medical data field 1200. In this example, the clinician has entered the attribute "productive"

in medical data field 1200. As illustrated, a second medical documentation set 1210 is displayed upon receiving the attribute. As before, the second medical documentation set may have a second set of medical documentation elements 1220 and a second set of medical data fields 1230. Each of the medical data fields may indicate that a response or attribute is either required or optional for the respective data field. Specifically, the user interface of FIG. 12 provides this indication by shading the medical data fields that require an attribute. In this example, medical data field 1232 is shaded and indicates that an attribute is required. In contrast, the lack of shading in medical data fields 1234 and 1236 indicate that an attribute is optional for these fields. Again, the labels of "required" and "optional" are used to indicate a hierarchal relationship between the medical data fields and do not necessarily "require" the entry of an attribute.

Figure 13:
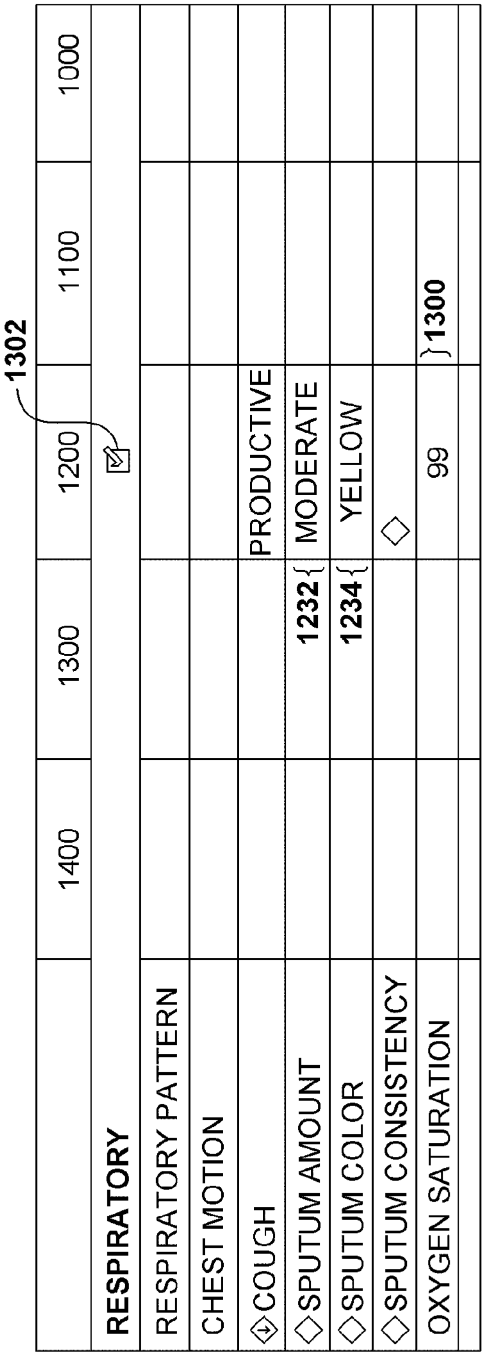
FIG. 13 is an illustrative screen display of an exemplary user interface for viewing a first and second medical documentation set that includes dynamic data, in accordance with an embodiment of the present invention.

By way of illustration only, FIG. 13 illustrates the resulting conditional logic user interface when the clinician enters an attribute for medical data field 1232 and optional medical data field 1234. Specifically, the clinician has entered "moderate" for data field 1232 and "yellow" for data field 1234. In addition, the figure illustrates that some of the medical data fields may include data that may be updated dynamically via communication with a local device, such as, a Bedside Medical Device. As discussed, this dynamic data may include physiological readings—such as, pulse rate, respiratory rate, oxygen saturation, body temperature, blood pressure, or the like. This dynamic data may be automatically triggered for updating once associated data fields include attributes. For example, once the clinician has entered assessment attributes for data fields 1232 and 1234, the user interface could receive and display any of this dynamic data. In this example, the dynamic data is associated with the medical documentation element "oxygen saturation."

Optionally, the user interface could prompt the clinician to query if the dynamic data should be updated for that particular data group. This query may include a signing component configured to receive an indication that a clinician is ready to update and document the dynamic data. For example, a clinician may provide this indication by selecting a selectable box 1302, icon, link, or the like. Upon receiving an indication that the clinician has signed the medical data, the user interface may be configured to enter this dynamic data in the respective dynamic fields. In addition, this dynamic data may be directly updated by a clinician entering an attribute for these dynamic fields.

Figure 14:
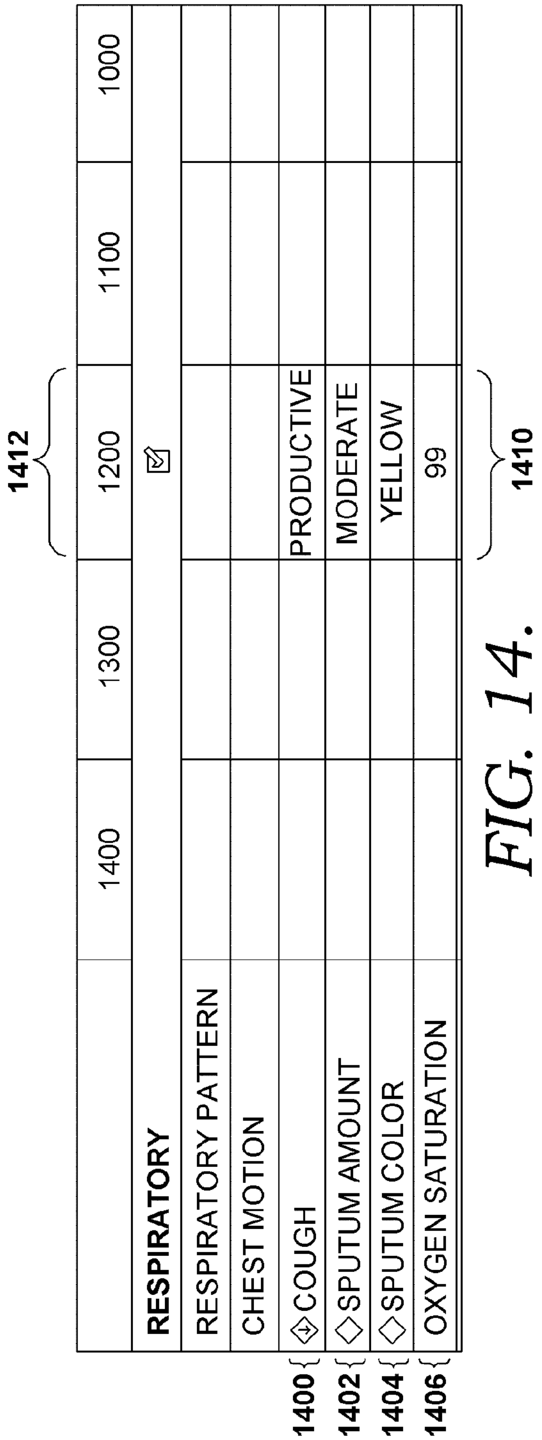
FIG. 14 is an illustrative screen display of an exemplary user interface for viewing an aggregated medical data group, in accordance with an embodiment of the present invention.

By way of illustration only, FIG. 14 illustrates the resulting conditional logic user interface once the data fields have been combined or aggregated to display only the medical data elements from the first medical documentation set and the second medical documentation set that include an attribute in the corresponding medical data fields. Specifically, first medical data element "cough" 1400 is displayed along with second medical data elements "sputum amount" 1402 and "sputum color" 1404. Referring to FIG. 13, an attribute for the data field associated with "sputum consistency" was not recorded, thus, this medical documentation element is not displayed in the user interface. Again, this provides a concise display and improves readability. In addition, first medical documentation element "oxygen saturation" 1406 which was dynamically updated is also displayed with a value of "99." As before, the medical data fields are displayed as a medical data group 1410 and are associated with a time stamp 1412.

By way of illustrates only, the exemplary displays of FIGS. 15-16 illustrate conditional logic examples of duplicating a row of medical data fields and documenting subsequent medical data fields in the duplicated rows. Specifically, FIG. 15 illustrates a first medical data group 1500 associated with a time stamp 1502. This medical data group 1500 has been duplicated and is illustrated by medical data group 1504 associated with a second time stamp 1506. It will be appreciated by those of ordinary skill in the art that such duplication can occur through "cut" and "paste" functionality.

In this example, the attribute for medical data field 1510 has been modified from an attribute of "moderate" to an attribute of "large." In addition, an attribute for the medical data field associated with the "cough" medical documentation element 1512 has not been entered in the medical data field 1514. This example illustrates that in one embodiment, copying a first medical documentation set does not require that all of the copied medical data fields have the same attributes included in the original data fields. Additionally, this example illustrate that dynamic data 1516 may be automatically updated via a medical device interface when medical data set 1504 was created. Specifically, the oxygen saturation in the second medical data group 1504 is "89" versus "99" in the first medical data group 1500.

By way of illustration only, FIG. 16 illustrates the resulting conditional logic user interface when a third medical data set 1600 is generated by copying either the first medical data set 1500 or the second medical data set 1504. As before, the third medical data set 1600 may be associated with a third time stamp 1602. Optionally, medical data set 1600 may include a newly generated data set and not a copy of a previous data set. In either case, the figure illustrates that when an attribute is entered in medical data field 1603 that is associated with medical data element "cough" 1604, the entire second set of medical data elements 1606 is displayed. Specifically, the "sputum amount", "sputum color", and "sputum consistency" elements. This is in contrast to FIG. 15, where only the copied medical data elements were displayed. Specifically, medical data element 1608 "sputum consistency" was not displayed with medical data set 1504 because it did not have an attribute in medical data set 1500. In contrast, "sputum consistency" 1608 is displayed with medical data set 1600 because an attribute was entered for the medical documentation element "cough" 1604 which is linked to the second medical documentation set. Thus, the entire second medical documentation set was displayed, in a similar manner as discussed regarding FIGS. 3-6. FIGS. 15 and 16 illustrate a few conditional logic examples of copying medical data groups and the resulting user interface. These examples are not intended to limit or display all of the possible user interfaces and functionality when copying data groups.

Figure 17:
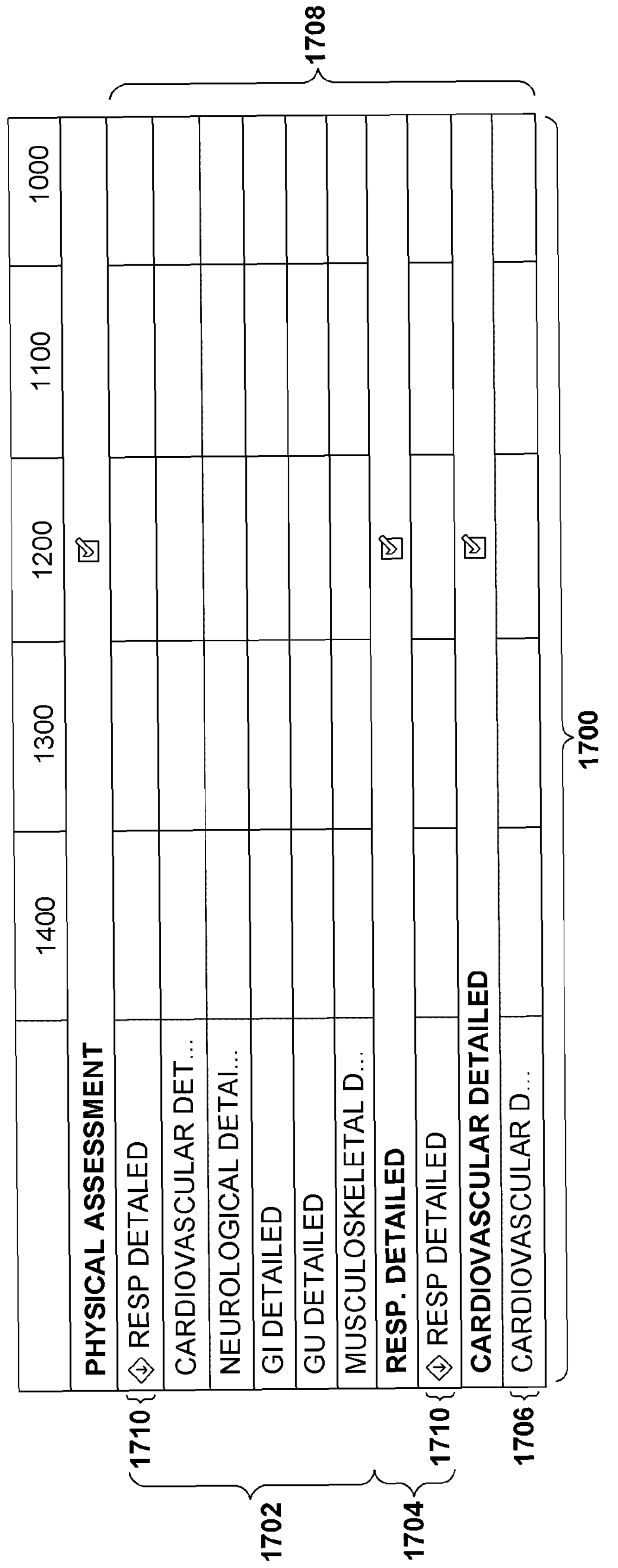
FIG. 17 is an illustrative screen display of an exemplary user interface for viewing a medical documentation element in two dynamic sections, in accordance with an embodiment of the present invention.

By way of illustration only, the exemplary conditional logic displays of FIG. 17 and 18 illustrate views for presenting a first medical documentation element in different sections of a first medical documentation set. Specifically, medical documentation set 1700 is illustrated with three dynamic sections. These dynamic sections include "physical assessment" 1702, "resp. detailed" 1704, and "cardiovascular detailed" 1706. Each of these dynamic sections includes medical documentation elements that are associated with medical data fields. The figure illustrates that the "resp. detailed" medical documentation element 1710 may be presented in more than one dynamic section. Specifically, "resp detail" 1710 is presented in the "physical assessment" section 1702 and the "respiratory detailed" section 1704.

By way of illustration only, FIG. 18 illustrates the resulting conditional logic user interface when the "resp detailed" element is triggered to display a second medical documentation set. Specifically, "resp detailed" 1710 and 1800 are indicated to be associated with a second documentation set by icon 1801. This icon is displayed in association with the "resp detailed" element in both dynamic sections. FIG. 18 illustrates the user interface once the clinician select either of the data fields 1806 or 1808. In this particular embodiment, the second medical documentation set is displayed in the second dynamic section as shown in FIG. 18. As before, this second medical documentation set includes a second set of medical documentation elements 1802 and a second set of medical data fields 1804. Once the second set of medical data fields 1804 are populated with attributes, the medical data field 1806 is displayed with a "Y" attribute.

The "Y" attribute is shorthand for "yes" and indicates that the medical data fields related to the medical documentation element have been documented. The "Y" attribute is also displayed in the "physical assessment" dynamic section in medical data field 1808. This may be useful for the scenario where the dynamic sections are not in close proximity to one another or on the same display presented to the clinician. Thus, it may indicate to the clinician that this second medical documentation set has been documented even though it is not currently displayed to the clinician. In addition, it may provide a hyperlink to this section and enable the clinician to simply click on the "Y" attribute to jump to the data fields that display the related attributes.

By way of illustration only, FIGS. 19 and 20 provide exemplary displays for modifying one of the medical data fields. Specifically, FIG. 19 illustrates three medical data groups 1900, 1902, and 1904. Each medical data group is associated with a time stamp 1906, 1908, 1910, respectively. As before, a first set of medical documentation element "cough" 1912 is presented with a second set of medical documentation elements. In this example, the second set of medical documentation elements include "sputum amount" 1914, "sputum color" 1916, and "sputum consistency" 1918. Referring to FIG. 20, as the clinician modifies medical data field 2000 from the "productive" to "nonproductive" attribute, the user interface provides an indication that such a modification has occurred by associating icon 2002 with data field 2000. The figure further illustrates, that in one embodiment of the user interface, the second set of medical documentation elements 2004, 2006, 2008, are not changed from their original values even though the first medical data field has been altered.

Figure 21:
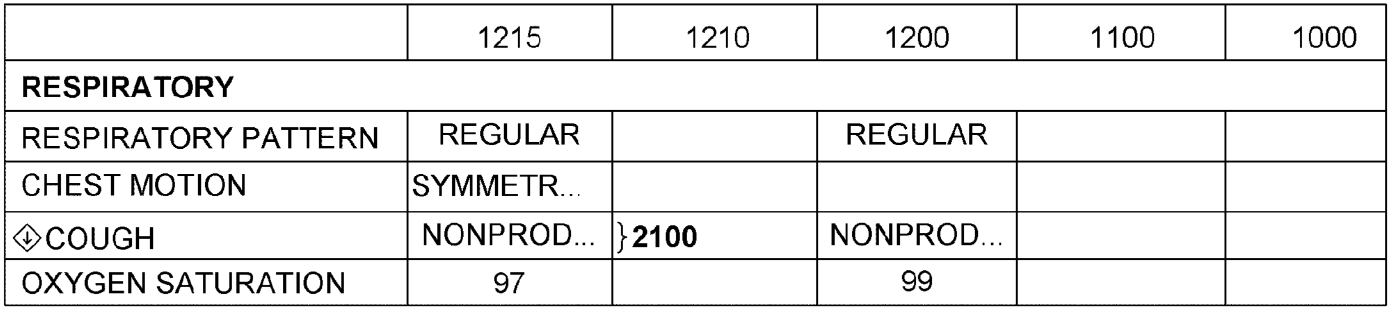
FIG. 21 is an illustrative screen display of an exemplary user interface for viewing a plurality of medical data groups, in accordance with an embodiment of the present invention.
Figure 22:
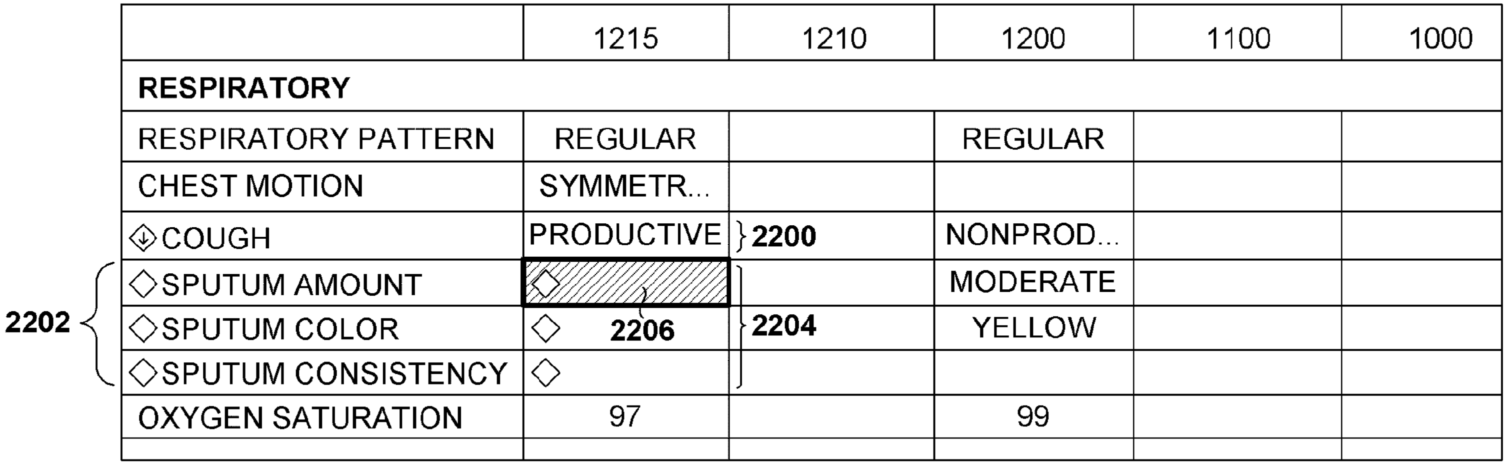
FIG. 22 is an illustrative screen display of an exemplary user interface, in accordance with an embodiment of the present invention, that may be utilized for changing one of the attributes of a medical data group.

By way of illustration only, FIGS. 21-22 illustrate a similar conditional logic modification to those illustrated in FIGS. 19-20 except that medical data field 2100 is changed to an attribute that triggers a second set of medical documentation elements and a second set of medical data fields. Specifically, referring to FIGS. 21 and 22, upon receiving a change in attribute from "nonproductive" 2100 to "productive" 2200, the user interface displays a second set of medical documentation elements 2202 and a second set of medical data fields 2204. Further, the medical data field 2206 associated with "sputum amount" is displayed as a required attribute as indicated by the shading.

By way of illustration only, FIGS. 23-25 provide exemplary conditional logic displays illustrating interfaces that enable a clinician to unchart attributes and medical data fields associated with either the first medical documentation elements or the second medical documentation elements. Specifically, FIG. 23 illustrates a first medical documentation element "cough" 2300 presented along with a second set of medical documentation elements 2302. In this example, the medical data fields associated with time stamp 2304 include two medical data fields 2306 and 2308 that are desired to be uncharted or removed from the display presented to the clinician.

By way of illustration only, FIG. 24 illustrates one possible conditional logic user interface that enables a clinician to unchart specific medical data fields. In this example, medical data fields 2306 is illustrated by row 2400 and medical data field 2308 is illustrated by row 2402. The unchart display may include a plurality of fields to inform a clinician with respect to details for the medical data that is displayed. For example, the display may include a "date and time" field 2404, an "item" description field which relates to the medical data element 2406, a "result" field 2408, a "reason" field 2410, and a "comment" field 2412. In addition, the display may include an "unchart field" 2414 that may be used for selecting which medical data fields to unchart.

Upon selecting which medical data field to unchart, the display may be updated as illustrated in FIG. 25. Medical data fields 2500 and 2502 now display an attribute that indicate the original attributes have been uncharted. Specifically, medical data fields 2500 and 2502 display "in error" or some other indicator for the attribute. For example, the attribute may be "uncharted", "removed", or some other indication that the attributes were charted at one time. In some embodiments, uncharting will require a reason for uncharting a medical label and/or documentation elements as illustrated by data field 2410. In such an embodiment, sufficient reasons might include charted on incorrect order, charted at incorrect time, charted on incorrect patient, and other. The uncharting interface may also enable a clinician to view result details for uncharted label. Such result details may include the medical label name and associated valid time period, the creator of the medical label, the status of the medical label, and the reason for the uncharted label.

By way of illustration only, the exemplary conditional logic display of FIG. 26 illustrates a view of a screen display that includes a plurality of dynamic groups. As before, the interface includes medical documentation elements 2600 and associated medical data fields 2602. The medical documentation elements may include a first set of medical documentation elements and a second set of medical documentation elements. FIG. 26 further illustrates three dynamic groups displayed in the user interface. Specifically, these dynamic groups include "right radial" 2604, "left subclavian" 2606, and "right subclavian" 2608.

Each dynamic group includes a medical documentation element that indicates it is linked to a second medical data field. For example, in the first dynamic group 2604, "line type" 2610 is displayed in association with icon 2612. Likewise in the second dynamic group "line type" 2614 is associated with icon 2616 and in the third dynamic group "line type" 2618 is associated with 2620. Each of the medical documentation elements 2610, 2614, 2618 indicates that they are linked to a second medical documentation set. However, unlike the examples illustrated in FIG. 18, the second medical documentation set are not linked or cross-referenced to one another. This means that entering attributes in one data field will not update or affect the attributes in the other data fields. In other words, even though they may display the same second medical documentation set if the same attribute is entered in the respective data fields, there will not be a link between the data fields in the displayed second documentation sets.

Referring to the first dynamic group 2604, an attribute of "arterial" is illustrated for the documentation element 2610. This attribute links to a second medical documentation element "collateral flow" 2622 that is displayed once the "arterial" attribute is received in the respective data field. The medical data field 2624 associated with the "collateral flow" element 2622 is further shown as a required attribute as indicated by the shaded data field. In contrast, the medical documentation element 2614 illustrated in the second dynamic group 2606 has an attribute that is not linked to a second medical documentation set. Specifically, the medical data field 2626 has a value of "PIV" and is not displaying a second medical documentation set.

In further contrast, medical documentation element 2618 illustrated in dynamic group 2608 has an attribute 2628 that is linked to a different second medical documentation set 2630 than the one linked to the "arterial" attribute in the first dynamic group 2604. In this example, the second medical documentation set 2630 includes medical documentation elements "pa line placement" 2632 and "pa wedge balloon" 2634. As with medical data field 2624, medical data field 2636 associated with medical data element 2632 is indicated as a required attribute as illustrated by the shading 2638 of the medical data field. This is in contrast to the unshaded medical data field 2638 associated with the "pa wedge balloon" element 2634.

The present invention has been described in relation to particular embodiments, which are intended in all respects to be illustrative rather than restrictive. Alternative embodiments will become apparent to those of ordinary skill in the art to which the present invention pertains without departing from its scope. From the foregoing, it will be seen that this invention is one well adapted to attain all the ends and objects set forth above, together with other advantages which are obvious and inherent to the system and method. It will be understood that certain features and sub-combinations are of utility and may be employed without reference to other features and sub-combinations. This is contemplated and within the scope of the claims.

What is claimed is:

1. One or more computer storage media having computer-executable instructions embodied thereon for performing a method in a clinical computing environment that guides a clinician to complete medical documentation, the method comprising:

presenting a first medical documentation set having a first set of medical documentation elements and a first set of medical data fields to indicate a medical aspect for which medical data is to be documented;

indicating that at least one of the medical documentation elements in the first set is linked to a second medical documentation set having a second set of medical documentation elements and a second set of medical data fields to indicate a medical aspect for which medical data is to be documented;

receiving a selection of at least one of the linked medical documentation elements in the first set;

presenting the second set of medical documentation elements and medical data fields in response to the selection;

receiving an attribute for at least one of the medical data fields in the first or second set;

aggregating the attributes received for the first and the second medical documentation sets into a medical data group; and presenting the medical data group including result details for any uncharted labels; and presenting an unchart display area configured to enable a user to remove attributes from the medical data group display area; wherein the unchart display area displays the attributes including one or more of a medical label name, a date/time, a creator and a status of the medical label and a reason for uncharting and wherein enabling a user to remove attributes comprises selecting an indicator indicating that the attributes is to be uncharted and wherein the reason for uncharting is subsequently displayed in the corresponding medical documentation element.

2. The one or more computer-readable media of claim 1, wherein indicating that at least one of the medical documentation elements in the first set is linked to a second medical documentation set comprises presenting an icon in association with at least one of the medical documentation elements presented in the first set or implementing a distinguishable font to display at least one of the medical documentation elements presented in the first set.

3. The one or more computer-readable media of claim 1, wherein the method further comprises indicating that an attribute is required for at least one of the medical data fields in the first set, the second set, or both sets.

4. The one or more computer-readable media of claim 3, wherein indicating that an attribute is required for at least one of the medical data fields comprises implementing an icon, a font, a color indicator, an audio signal, or combination thereof to distinguish the required medical data field from other medical data fields.

5. The one or more computer-readable media of claim 1, wherein receiving a selection of at least one of the linked medical documentation elements in the first set comprises receiving an attribute for one of the medical data fields in the first set.

6. The one or more computer-readable media of claim 1, wherein receiving a selection of at least one of the linked medical documentation elements in the first set comprises receiving a predetermined attribute that triggers presenting the second set of medical documentation elements.

7. The one or more computer-readable media of claim 1, wherein receiving an attribute for at least one of the medical data fields in the first or second sets comprises displaying a list associated with the medical data fields and receiving a selection from the list.

8. The one or more computer-readable media of claim 1, wherein receiving an attribute for at least one of the medical data fields in the first or second sets comprises receiving an attribute that falls above or below a predetermined threshold.

9. The one or more computer-readable media of claim 1, wherein the method further comprises:

associating the medical data group with a first time stamp;

duplicating the medical data group to create a second medical data group, wherein the medical data group includes assessment data, and duplicating the medical group includes copying the assessment data from the medical data group to the second medical data group;

associating the second medical data group with a second time stamp; and displaying the second medical data group.

10. The one or more computer-readable media of claim 9, wherein the medical group includes dynamic data and duplicating the dynamic data includes updating the dynamic data in the second medical data group via a medical device interface.

11. The one or more computer-readable media of claim 1, wherein the method further comprises:

indicating that at least one of the medical documentation elements in the second medical document set is linked to a third medical documentation set having a third set of medical documentation elements and a third set of medical data fields to indicate a medical aspect for which medical data is to be documented;

receiving a selection of at least one of the linked medical documentation elements in the second set;

presenting the third set of medical documentation elements and medical data fields in response to receiving the selection;

indicating that an attribute is required for at least one of the medical data fields in the third set; and receiving an attribute for at least one of the medical data fields in the first, second, or third set.

12. The one or more computer-readable media of claim 1, wherein presenting a first medical documentation set comprises presenting a first medical document set having at least two sections, wherein the link to the second medical documentation set is displayed in both sections.

13. The one or more computer-readable media of claim 1, wherein presenting a first medical documentation set comprises displaying a first medical document set having a plurality of sections, each section having a link to a separate second medical documentation set.

14. The one or more computer-readable media of claim 1, wherein receiving an attribute for at least one of the medical data fields in the first or second set comprises receiving medical data within the medical data fields, wherein the medical data is documented at a point of care in association with medical care provided to a patient.

15. A user interface embodied on at least one computer storage media, the user interface facilitating the completion of medical documentation, the user interface comprising; a display area displayed on the display of a computer device comprising:

a first medical documentation set display area configured to display a first medical documentation set having a first set of medical documentation elements and a first set of medical data fields to indicate a medical aspect for which medical data is to be documented;

a trigger indicator, selection of which initiates an association between the first medical documentation set and a second medical documentation set;

a second medical documentation set display area configured to display a second medical documentation set having a second set of medical documentation elements and a second set of medical data fields associated with the first medical documentation set;

a medical data group display area configured to receive attributes associated with the first and the second medical documentation sets and aggregate the attributes into a medical data group; and an unchart display area configured to enable a user to remove attributes from the medical data group display area; wherein the unchart display area displays the attributes including one or more of a medical label name, a date/time, a creator and a status of the medical label and a reason for uncharting and wherein enabling a user to remove attributes comprises selecting an indicator indicating that the attribute is to be uncharted and wherein the reason for uncharting is subsequently displayed in the corresponding medical documentation element.

16. The user interface of claim 15 further comprising a modification display area configured to indicate that an attribute in the medical data group was modified from an original entry.

17. The user interface of claim 15 further comprising a required field display area configured to indicate that an attribute is required for a medical data field in the first or second medical documentation set.

18. The user interface of claim 15 further comprising a multiple section display area configured to display a plurality of sections, wherein at least two of the sections have at least one first medical documentation set display area, at least one trigger display area, at least one second medical documentation set display area, and at least one medical data group display area.

19. One or more computer storage media having computer-executable instructions embodied thereon for performing a method in a clinical computing environment that guides a clinician to complete medical documentation, the method comprising:

presenting a first medical documentation set having a first set of medical documentation elements and a first set of medical data fields to indicate a medical aspect for which medical data is to be documented;

indicating that at least one of the medical documentation elements in the first set is linked to a second medical documentation set having a second set of medical documentation elements and a second set of medical data fields to indicate a medical aspect for which medical data is to be documented;

receiving a selection of at least one of the linked medical documentation elements in the first set;

presenting the second set of medical documentation elements and medical data fields in response to the selection;

receiving an attribute for at least one of the medical data fields in the first or second set;

aggregating the attributes received for the first and the second medical documentation sets into a medical data group;

associating the medical data group with a first time stamp and displaying the medical data group;

duplicating the medical data group to create a second medical data group, wherein the medical data group includes assessment data and dynamic data, and duplicating the assessment data includes copying the assessment data from the medical data group to the second medical group and duplicating the dynamic data includes updating the dynamic data in the second group via a medical device interface;

associating the second medical data group with a second time stamp and displaying the second medical data group; and enabling a clinician to view result details for any uncharted labels; and presenting an unchart display area configured to enable a user to remove attributes from the medical data group display area; wherein the unchart display area displays the attributes including one or more of a medical label name, a date/time, a creator and a status of the medical label and a reason for uncharting and wherein enabling a user to remove attributes comprises selecting an indicator indicating that the attribute is to be uncharted and wherein the reason for uncharting is subsequently displayed in the corresponding medical documentation element.

* * * * *